US012580768B2

(12) United States Patent
Arkoff et al.

(10) Patent No.: US 12,580,768 B2
(45) Date of Patent: Mar. 17, 2026

(54) SYSTEM AND METHOD FOR DECENTRALIZED PERSONA AGENT GOVERNANCE IN REGULATED ENVIRONMENTS USING LARGE LANGUAGE MODELS

(71) Applicant: OneSource Solutions International, Inc., Sudbury, MA (US)

(72) Inventors: Harold Arkoff, Sudbury, MA (US); Vedran Jukic, Trieste (IT)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/276,173

(22) Filed: Jul. 22, 2025

(65) Prior Publication Data

US 2026/0019268 A1     Jan. 15, 2026

Related U.S. Application Data

(63) Continuation-in-part of application No. 18/680,985, filed on May 31, 2024, now Pat. No. 12,380,144.

(51) Int. Cl.
H04L 9/32 (2006.01)
G16H 10/60 (2018.01)

(52) U.S. Cl.
CPC ........... H04L 9/3234 (2013.01); G16H 10/60 (2018.01)

(58) Field of Classification Search
CPC ........ H04L 9/3234; G06N 20/00; G06N 5/02; G16H 10/60
See application file for complete search history.

(56) References Cited

U.S. PATENT DOCUMENTS 12,316,753 B1 *   5/2025   Dahme ................. H04L 9/0891
12,468,510 B1 *  11/2025   Kuperman ............... G06F 8/77
(Continued)

OTHER PUBLICATIONS

Phiri, Charles Chimwemwe. "Creating Characteristically Auditable Agentic AI Systems." Proceedings of the Intelligent Robotics FAIR 2025. 2025. 1-14. (Year: 2025).*
(Continued)

*Primary Examiner* — Kari L Schmidt
(74) *Attorney, Agent, or Firm* — IP Consulting Group; Michael Razavi; Alfred F. Hoyte, Jr.

(57)     ABSTRACT

A decentralized mesh-network platform provides real-time governance, supervision, and audit of large-language-model persona agents in regulated environments such as healthcare. Each computing node hosts processor circuitry, memory, a network interface, and an integrated suite comprising a User-Prompt Interface, Metadata Filter & Enrichment Engine, Persona Role Constructor, Policy Constraint Engine, gating logic module, Supervisor Review Interface, Session Memory Governance Module, Audit Logging Subsystem, cryptographically linked audit ledger, and Fallback Control Module. Devices communicate over a peer-to-peer channel, exchange role-switch tokens, and merge local ledgers into a composite audit graph when connectivity returns. The architecture supports continuous compliance and resilient operation across institutional boundaries, network partitions, and device failures, enabling conversational interaction with heterogeneous medical data while maintaining rigorous credential lineage, policy oversight, and forensic traceability.

20 Claims, 12 Drawing Sheets

(56) References Cited

U.S. PATENT DOCUMENTS

| | | | |
|---|---|---|---|
| 12,483,411 B1 * | 11/2025 | Chen | H04L 9/3213 |
| 12,488,874 B1 * | 12/2025 | Christopherson | G16H 20/60 |
| 2021/0064643 A1 * | 3/2021 | Folland | G06F 16/338 |
| 2023/0140553 A1 * | 5/2023 | Mahindru | G06Q 10/06393 |
| | | | 705/7.37 |
| 2024/0320476 A1 * | 9/2024 | Chandrasekaran | G06N 20/00 |
| 2024/0420846 A1 * | 12/2024 | Hernandez | G16H 20/70 |
| 2025/0094619 A1 * | 3/2025 | Pasumarthi | G06F 21/6227 |
| 2025/0111940 A1 * | 4/2025 | Dent | G06T 13/40 |
| 2025/0131375 A1 * | 4/2025 | Maggiore | G06F 3/017 |
| 2025/0148356 A1 * | 5/2025 | Weidner | G06N 5/022 |
| 2025/0259082 A1 * | 8/2025 | Crabtree | G06N 3/047 |
| 2025/0292900 A1 * | 9/2025 | Wen | G16H 50/20 |
| 2025/0294061 A1 * | 9/2025 | Arkoff | H04L 63/20 |
| 2025/0307436 A1 * | 10/2025 | Doyle | H04L 9/50 |
| 2025/0328341 A1 * | 10/2025 | Gutierrez | G06F 40/166 |
| 2025/0335707 A1 * | 10/2025 | Xu | G06F 21/62 |
| 2025/0373432 A1 * | 12/2025 | Arkoff | G06F 21/6254 |
| 2025/0378108 A1 * | 12/2025 | Orth | G06F 16/38 |

OTHER PUBLICATIONS

Z. Liu et al., "Comprehensive Evaluation of AI Hallucination and Novel UV-Oriented Framework toward Safe and Trustworthy AI," 2024 7th International Conference on Universal Village (UV), Boston, MA, USA, 2024, pp. 1-136. (Year: 2024).*

Alsagheer, Dana, Lei Xu, and Weidong Shi. "Decentralized machine learning governance: Overview, opportunities, and challenges." IEEE Access 11 (2023): 96718-96732. (Year: 2023).*

* cited by examiner

SYSTEM AND METHOD FOR DECENTRALIZED PERSONA AGENT GOVERNANCE IN REGULATED ENVIRONMENTS USING LARGE LANGUAGE MODELS

CROSS-REFERENCE TO RELATED APPLICATIONS

This application is a Continuation-in-Part of U.S. application Ser. No. 18/680,985 (filed May 31, 2024, entitled "System and Method for Medical Data Governance Using Large Language Models"), which itself is a continuation of U.S. application Ser. No. 18/417,511 (filed Jan. 19, 2024, now U.S. Pat. No. 12,001,464, issued Jun. 4, 2024).

STATEMENT REGARDING FEDERALLY SPONSORED RESEARCH OR DEVELOPMENT

None.

FIELD OF TECHNOLOGY

The invention relates to artificial-intelligence systems deployed in regulated domains—particularly healthcare—and, more specifically, to real-time decentralized governance, supervision and audit of persona agents (synthetic conversational or decision-making interfaces powered by large language models or similar AI technologies).

BACKGROUND

In recent years, the proliferation of digital health records, coupled with the advancements in artificial intelligence and natural language processing, has created a need for governance of healthcare data. Healthcare systems worldwide are generating vast volumes of sensitive medical data, ranging from patient records and diagnostic imaging to genomic information, presenting both opportunities and challenges in its governance, security, and accessibility. The management and governance of such medical data have become increasingly critical in modern healthcare systems.

Traditional approaches to medical data governance often face challenges in maintaining data integrity, protecting patient confidentiality, complying with regulatory requirements, and transmitting data sharing effectively in facilitating empowered agencies. The sheer complexity and sensitivity of medical information present unique challenges that require innovative solutions for improved governance. The need for robust processes to ensure data integrity, confidentiality, and compliance with regulatory frameworks has never been greater.

Furthermore, the evolution of medical data management has been marked by challenges in accessing and querying disparate databases (or repositories) while ensuring strict compliance with regulatory frameworks governing sensitive healthcare information. Traditional systems often necessitate rigid query formats and specific languages, impeding seamless access to comprehensive medical data. Therefore, there is also a requirement for a system that can process user queries in their preferred language (say English, Spanish, and the like) and also in a conversational style as compared to formatted queries that may be difficult for some users to understand and write, thereby restricting them from using the available medical data.

Traditional AI deployments centralize critical processing in remote data-centers. In clinical settings this creates single points of failure: an outage can halt medication-dispensing queues, pause radiology reports or suppress alarm routing, jeopardizing patient safety and statutory compliance.

Modern regulations (HIPAA, GDPR, EU AI Act, NIST AI-RMF) demand continuous enforcement of credential lineage, policy gating, geolocation constraints, output supervision and cryptographically linked audit. Centralized architectures cannot satisfy those requirements when bedside devices must operate autonomously during network partitions.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY OF THE DISCLOSURE

The present disclosure describes an integrated platform that governs, secures, and exploits medical data through large-language-model (LLM) technology and a decentralized mesh of edge devices. Although certain examples may describe a mesh or distributed arrangement of computing nodes, it should be understood that the invention is not limited to a particular network or deployment structure. In some embodiments, all system functions may be performed on a centralized server or cloud instance, with edge devices acting as thin clients. In other embodiments, a hub-and-spoke model, hybrid cloud/edge topology, or even a single-node implementation may be employed. All such arrangements are considered within the scope of the present invention. The system accepts conversational queries in any supported language, retrieves pertinent information from heterogeneous medical repositories, and enforces real-time privacy, credential, and policy constraints-thereby elevating patient care, accelerating research, and improving population-level analytics.

In modern healthcare, data is voluminous, diverse, and highly sensitive, spanning electronic health records, diagnostic imaging, genomics, and continuous telemetry from wearable or bedside devices. The sheer scale and fragmentation of these resources hinder interoperability, while regulatory frameworks such as HIPAA, GDPR, the EU Artificial-Intelligence Act, and emerging NIST guidelines impose strict requirements for privacy, security, and auditable usage. Existing centralized AI architectures struggle to meet these demands, because any outage or network partition can interrupt critical workflows and obscure real-time compliance status.

To overcome these challenges, the disclosed system fuses advanced natural-language processing with a robust governance pipeline. When a user or automated workflow submits a query, the platform enriches that prompt with structured metadata capturing initiator identity, credential lineage, institutional affiliation, geographic location, model-instance provenance, privacy flags, and current policy context. An LLM-driven persona agent—a synthetic conversational or decision-making entity bound by the captured metadata—is instantiated directly on a computing node such as a bedside terminal or mobile workstation. The computing node could be any processor-based system, including but not limited to edge computing devices (hardware device, including but not limited to bedside terminals, workstations, IV pole modules, or mobile devices), centralized servers, virtual machines, or cloud computing instances, deployed on-premises, in a public or private cloud, or in a hybrid environment, capable of locally instantiating, executing, and supervising persona agents, enforcing policy, maintaining audit records, and participating in a mesh network. A policy-constraint engine evaluates every agent action in real time; if a request exceeds authorized scope or presents regulatory ambiguity, the operation is automatically gated to a supervisory interface for human or digital review. All approvals, denials, delegations, and memory-window events are hashed and appended to a tamper-evident, cryptographically linked audit ledger.

In an embodiment, computing nodes cooperate in a peer-to-peer mesh that balances workload and sustains autonomous operation whenever cloud connectivity is lost. A fallback control module continuously monitors computing node availability and operational health. Upon detecting the unavailability or failure of a first computing node, the module triggers a failover procedure. The module issues a cryptographically signed role-switch token when a node becomes unavailable, allowing an authorized peer to resume active sessions without breaking credential lineage or audit continuity. To simply put, a role-switch token is a cryptographically signed data artifact transmitted between mesh nodes to authorize and document the transfer of operational responsibilities, session memory, and delegation chain during failover or mesh topology adjustment. For cross-institutional hand-offs the platform generates federated compliance tokens that encapsulate the full delegation chain, credential set, policy snapshot, and privacy context; a receiving institution validates the token before permitting remote agent execution, ensuring continuous, verifiable compliance across organizational boundaries.

By uniting conversational LLM access, fine-grained policy enforcement, edge-level fault tolerance, and end-to-end auditability, the disclosure sets a new benchmark in healthcare informatics. It empowers clinicians and researchers to interrogate complex data landscapes effortlessly, maintains continuous evidence for regulators, and eliminates single points of failure that have historically limited AI deployment in mission-critical, compliance-sensitive environments.

The invention may be practiced in any network or deployment topology, including but not limited to decentralized mesh networks, distributed clusters, centralized server systems, hub-and-spoke models, cloud-based architectures, hybrid arrangements, or single-node deployments. The described modules and functionalities may be hosted and executed on any combination of physical or virtual computing nodes, regardless of network organization.

DETAILED DESCRIPTION OF THE DISCLOSURE

Figure 1:
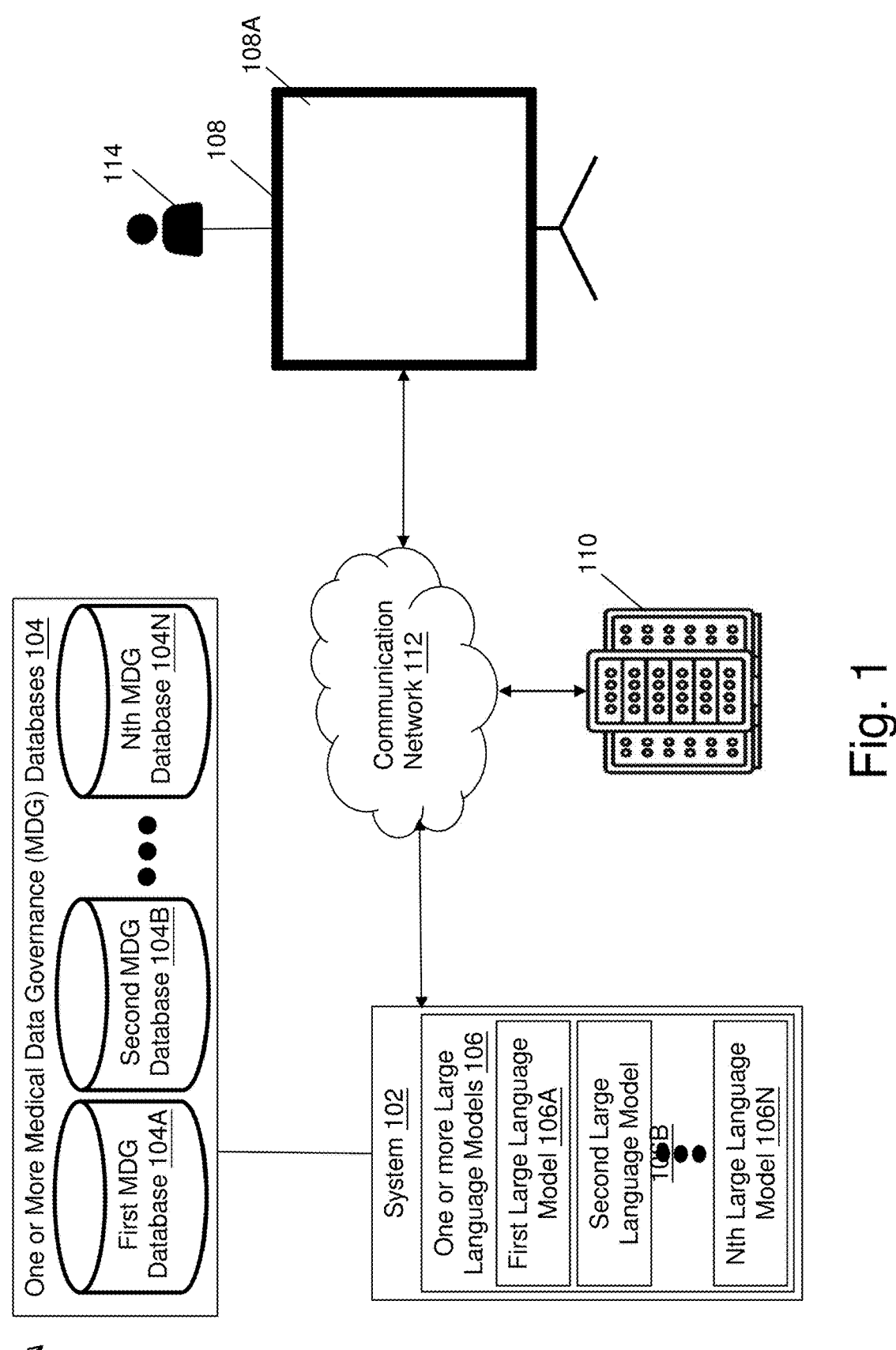
FIG. 1 is a block diagram that illustrates an exemplary environment for medical data governance using large language models, in accordance with an exemplary embodiment of the disclosure.

Modern hospitals, ambulances, outpatient clinics, and other compliance-sensitive environments increasingly rely on artificial-intelligence assistants to streamline clinical decision-making, automate documentation, and coordinate care across institutional and jurisdictional boundaries. Various aspects of the disclosure may be found in a method and system for medical data governance using large language models. With the digitization in the medical field, the management and governance of medical data have become increasingly critical in modern healthcare systems. Specifically, with the digitization of patient records, advancements in medical technology, and the ever-growing volume of healthcare data, ensuring the security, integrity, and responsible use of this information has emerged as a pivotal concern. Traditional methods of medical data management often encounter challenges in maintaining data accuracy, protecting patient privacy, adhering to regulatory requirements, and facilitating efficient data sharing among authorized entities. The complexity and sensitivity of medical data pose unique challenges that necessitate innovative solutions for robust governance.

The principal impediment to the advancement and adoption of artificial intelligence (AI) within critical care environments is the absence of a robust infrastructure and research tools for data capable of gathering high-frequency, unfiltered, and time-synchronized data directly from all available medical devices associated with patients, and before they get filtered, reduced and stripped from metadata and stored in the clinical patient record. Here, metadata is any structured data associated with each prompt or agent session, including but not limited to initiator identity, credential information, institutional affiliation, geographic location, language model instance accreditation, privacy flags, risk classification, delegation chain data, and policy context. Here, credential information is any data or digital artifact (e.g., digital certificate, role assignment, user identifier) that attests to the authority, permissions, or professional qualification of an initiator or agent. Institutional Affiliation is associated with any information identifying the organization, hospital, clinic, department, or regulated entity with which the initiator or persona agent is associated. Geographic Location specifies a location data for an initiator or computing node, including (but not limited to) GPS coordinates, physical address, or region code, as relevant for policy enforcement or jurisdictional compliance. Language Model Instance Accreditation is a digital identifier or attestation associated with the specific large language model (LLM) or AI model instance employed by the persona agent, used for provenance, version control, or regulatory validation. Privacy Flags are metadata fields indicating the privacy classification, consent status, or regulatory requirements applicable to a prompt, agent session, data type, or output. Delegation Chain is a sequential record of all entities-whether human users or persona agents-through which authority, credentials, or session control have been delegated or transferred during a workflow or agent session. Simply put, the main reason AI isn't used more widely in critical care is because of the lack of infrastructure to collect and process the data necessary for training and using AI systems. This data needs to be collected in real-time, without any unnecessary transformations, from all the medical devices that patients use. Additionally, it may be of utmost importance that this data is organized and normalized in a way that AI systems can understand and use effectively.

As used herein, a "computing node" refers to any processor-based hardware or virtual instance capable of executing the modules and performing the methods described herein. This includes, but is not limited to, edge computing devices, centralized servers, virtual machines, or cloud computing instances, whether deployed on-premises, in a public or private cloud, or as part of a hybrid environment. A computing node may be implemented as a physical device, a virtual machine, a software container, or any equivalent computational entity suitable for performing the claimed invention's functions.

In the realm of medical imaging, the proliferation of unfiltered imaging data accompanied by diagnostic information and patient outcomes has fostered the development of numerous AI applications founded on machine learning algorithms. The medical imaging field is a good example of how AI can be used to improve patient care. The AI models may have been trained on large datasets of unfiltered medical images to identify diseases and predict patient outcomes. However, to achieve similar results in critical care environments, there is a requirement to develop a better way to collect and process data from medical devices.

In recent years, with the advent of advanced technologies, artificial intelligence (AI)-based solutions, in particular, have demonstrated their potential in transforming the landscape of medical data governance. Specifically, large language models (LLMs), powered by deep learning algorithms, have emerged as transformative tools capable of understanding, processing, and generating human-like text at an unprecedented scale and depth. In the healthcare sector, the application of the LLMs presents a compelling opportunity to revolutionize medical data governance. By harnessing the power of these LLMs, there exists the potential to address key challenges in data quality enhancement, privacy preservation, regulatory compliance, and semantic understanding and insights.

Figure 12:
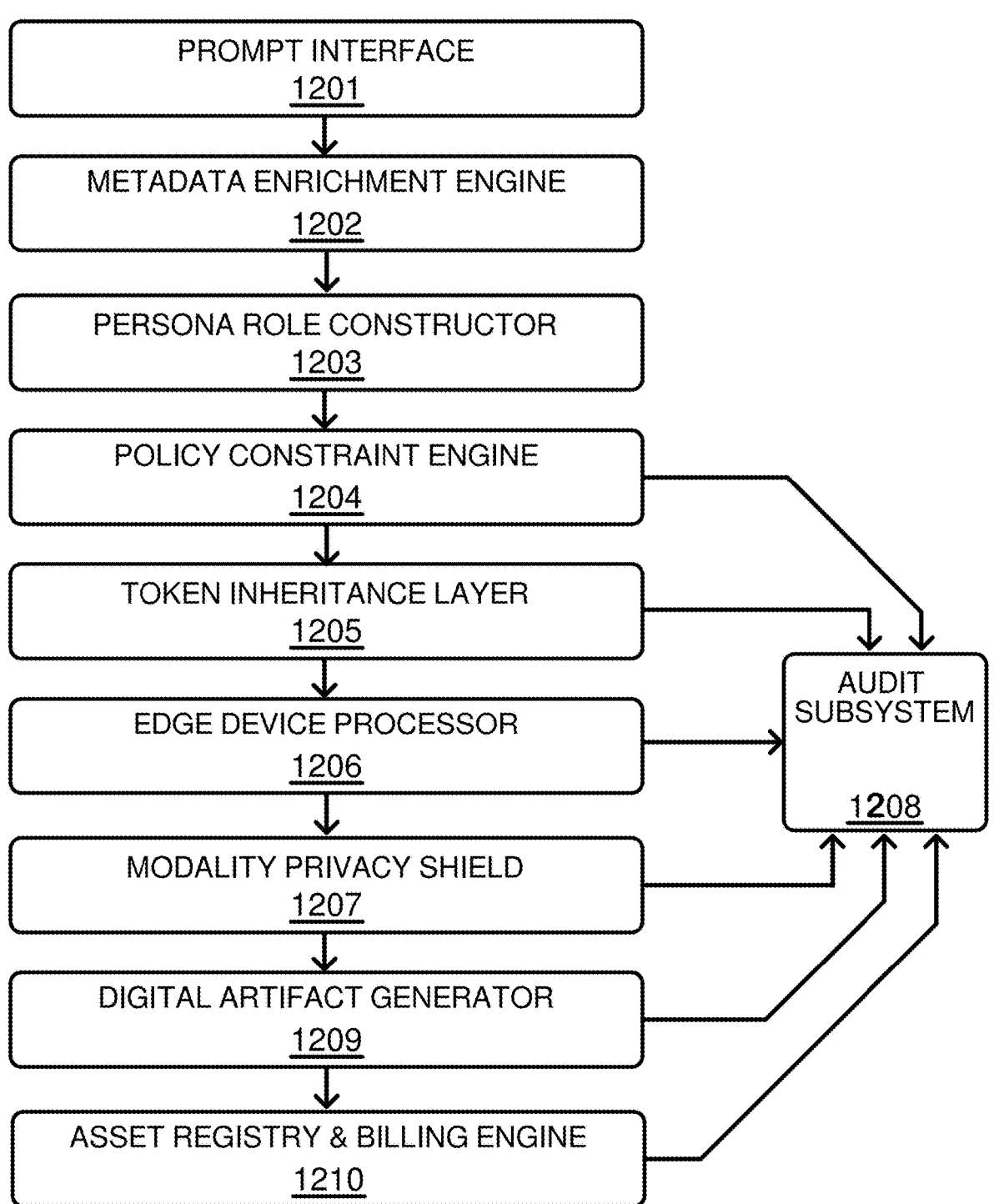
FIG. 12 presents an integrated system architecture combining prompt ingress, metadata enrichment, policy-constraint engine, edge-device runtime, privacy shield, distributed audit ledger and asset-registry modules.

To address these challenges, the present invention provides a decentralized, mesh-based governance architecture—depicted in FIG. 12—that instantiates persona agents in response to prompts, enriches those prompts with exhaustive metadata, enforces policy in real time, gates high-risk outputs for supervisory review, maintains a cryptographically linked audit ledger that is a sequence of audit records where each record is digitally signed and cryptographically bound to its predecessor(s), forming an immutable chain resistant to unauthorized modification, and enables seamless, tokenized hand-off of authority across institutions. A prompt is any input, query, or instruction provided to the system by a human user or artificial intelligence agent, intended to initiate a workflow, request information, or trigger a persona agent session. Persona agent is a software entity, implemented as a conversational or decision-making interface, powered by a large language model (LLM) or similar artificial intelligence. To simply put, an audit ledger refers to a component or module configured to generate, store, and maintain tamper-evident, cryptographically linked records of system events, including prompt receipt, agent instantiation, policy evaluation, delegation, gating, session memory events, and outputs. The audit ledger refers to the persistent, ordered collection of such audit records. In essence, the system guarantees that every AI-driven interaction is provably compliant, traceable and resilient, from bedside terminal to remote tertiary-care partner, even in the face of node failure or network partition. The disclosure proposes a system and method that harnesses the capabilities of LLMs to revolutionize medical data governance. By integrating these LLMs into the fabric of healthcare data management, the innovation outlined herein aims to establish a robust framework for ensuring data accuracy, privacy, regulatory compliance, and enhanced insights extraction while navigating the complexities inherent in managing vast volumes of sensitive medical information.

The system incorporates a memory governance module that enforces a session memory window, limiting the agent's retention of context in accordance with policy or privacy requirements, and triggering expiration or reset upon completion, credential revocation, or policy change. All agent instantiations, actions, delegation events, policy states, memory events, and supervisory decisions are logged by an audit subsystem, which maintains a cryptographically linked, tamper-evident audit record. The audit system constructs a composite audit graph, capturing the full lineage of credentials, policy versions, geo-location, LLM instance details, privacy flags, and digital signatures, supporting forensic and regulatory traceability. Composite audit graph is a structured, cryptographically linked data structure that aggregates audit records, delegation chains, credential lineage, policy states, and supervisory decisions for each persona agent session or workflow.

Medical Data Governance may be important for several reasons, including protecting the privacy of patients, ensuring the quality of data, and promoting the ethical use of data. For example, medical data governance helps to protect the privacy of patients by ensuring that their data is collected, stored, and used responsibly. This includes de-identifying data before it is shared with researchers or other third parties. Also, medical data governance helps to ensure the quality of data by ensuring that it is collected, stored, and transmitted consistently and accurately. This helps to reduce the risk of errors and bias in research findings. Furthermore, medical data governance helps to promote the ethical use of data by ensuring that it is used for legitimate purposes and that it is not shared with unauthorized parties. This helps to protect the public trust and to ensure that research is conducted responsibly.

FIG. 1 is a block diagram that illustrates an exemplary environment for medical data governance using large language models, in accordance with an exemplary embodiment of the disclosure. Referring to FIG. 1, there is shown a network environment 100, which may include a system 102, one or more medical data governance (MDG) databases 104, one or more (LLMs) 106, a user device 108 that includes a display device 108A, a server 110, and a communication network 112. The one or more MDG databases 104 may include a first MDG database 104A, a second MDG database 104B, up to an Nth MDG database 104N. Similarly, the one or more LLMs 106 may include a first LLM 106A, a second LLM 106B, a third LLM 106C, up to an Nth LLM 106N. With reference to FIG. 1, there is further shown a user 114 associated with the user device 108.

The system 102 may comprise suitable logic, circuitry, interfaces, and/or code that is configured to receive a user input including at least one search query to retrieve first medical data from the one or more MDG databases 104. The first medical data corresponds to the information that may be requested by the user. In some embodiments, the system 102 may be further configured to apply the one or more LLMs 106 on the received at least one search query. The system 102 may be further configured to determine metadata associated with the at least one search query based on the application of the one or more LLMs 106 on the received search query. The system 102 may be further configured to query at least the first MDG database 104A of the one or more MDG databases 104 based on the determined metadata to retrieve the first medical data. The system 102 may be further configured to output the retrieved first medical data. Examples of the system 102 may include, but are not limited to, a computing device, a mainframe machine, a server, a computer workstation, a smartphone, a cellular phone, a mobile phone, a gaming device, and/or a consumer electronic (CE) device with image processing capabilities.

In an embodiment, the system 102 may correspond to an MDG system that may enable medical data governance (MDG). As discussed above, MDG provides a true source of data that can highlight the schedule of medical treatments and provides tools for rescheduling feedback, contacting and receiving feedback from patients/physicians/healthcare professionals thus introducing general system flexibility through the use of lean process and six sigma methods. MDG leverages modern communication methods (phone apps, emails, web services, etc.) and easily links patient's physicians, or other healthcare professionals to the scheduled use of medical devices. After unexpected events that may cause a miss in scheduled operations, the MDG may create a backup schedule to pre-emptively fill the gaps and may facilitate healthcare and schedule professionals to optimize machine time usage. This could create a new marketplace for priority services for those patients who opt for it.

Also, MDG may enable patients/users and or institutions to monetize their vital, medically relevant, patient data collected during the stay inside the healthcare institution, as well through the extended data collected over some time in multiple stays or spot measurements in healthcare institutions. Patients may be able to establish a relationship with a third party (such as a drug manufacturer, independent drug trial projects, undisclosed trials to the institution) and provide to the third party normalized data collected, organized, and provided by the MDG used by the healthcare institution, and provided to the patient in a different standardized format, even in near real-time. The institution might not be aware of the final user of the patient data. MDG can create additional revenue for the institution by charging such a service per patient and data processed. MDG can track and trace data usage per patient and assets. MDG through the export of all specific, validated clinical data, and medical relevant data, could create a new data-based economy.

Furthermore, MDG manages patient consent and approval, or notification for the use of the patient data for second opinions, medical treatments, specific research, validation projects, and educational purposes. Specific patient or user data is previously screened based on always updated, public, generic, anonymous metadata (for example: sex, age, days in hospital, normalized data content and length: heart rate, respiration rate, drugs, etc.). MDG can handle patient consent using modern communication methods (phone apps, emails, web services, etc.) and provide patient consent for his data to be used in a specific research or validation project, with or without compensation. MDG can provide patient consent and access to the data to specific users, like doctors, physicians, and other specific medical professionals. MDG can provide specific code associated with the data, that, based on necessity, can provide, if granted by the user or proxy consent, protected personal identification, family relations, or other protected personal data. MDG may allow for third-party statistical analysis (research) on the whole population dataset, without exporting or providing data to the third party, but rather comparing the result to the legally available consent subset group. A statistically relevant result might indicate a minimal group of statistically significant subset of data to search consent and optimize the time for valid and repeatable datasets.

Each of the one or more MDG databases 104 may correspond to a structured collection of organized information stored electronically in a way that enables easy access, retrieval, and manipulation of medical data. The one or more MDG databases 104 may serve as a centralized database where the medical data may be systematically arranged into tables, records, and fields, following a predefined data model. The one or more MDG databases 104 may be designed to efficiently manage vast amounts of information, allowing users to perform queries, insert new data, update existing records, and delete information based on specific requirements. In an embodiment, the one or more MDG databases 104 may correspond to a storage system associated with the MDG. Examples of different types of the one or more MDG databases 104 may include, but are not limited to, a relational database, a non-relational database, a document database, and a graph database.

Each of the one or more LLMs 106 may correspond to a sophisticated artificial intelligence (AI) system trained on vast amounts of text data, capable of understanding, generating, and processing human-like language at an extensive scale. Each of the one or more LLMs 106 models utilizes deep learning techniques, particularly transformer architectures, enabling them to grasp context, syntax, semantics, and even nuances in language usage. The primary function of the one or more LLMs 106 may involve, but is not limited to, natural language processing tasks like text generation, translation, summarization, and sentiment analysis. Each of the one or more LLMs 106 may learn to predict and generate text by analysing patterns and relationships within the massive corpus of text they've been trained on. Examples of different types of the one or more LLMs 106 may include, but are not limited to, a Transformer-Based Model, a Bidirectional Encoder Representations from Transformers (BERT) model, a Generative Pre-trained Transformer (GPT) model, a Unified Language Model, and a Text-to-Text Transfer Transformer (T5) model.

In an embodiment, each of the one or more LLMs 106 may include a neural network that may be a computational network or a system of artificial neurons, arranged in a plurality of layers, as nodes. The plurality of layers of each of the neural network may include an input layer, one or more hidden layers, and an output layer. Each layer of the plurality of layers may include one or more nodes (or artificial neurons). Outputs of all nodes in the input layer may be coupled to at least one node of hidden layer(s). Similarly, inputs of each hidden layer may be coupled to outputs of at least one node in other layers of the corresponding neural network. Outputs of each hidden layer may be coupled to inputs of at least one node in other layers of the corresponding neural network. Node(s) in the final layer may receive inputs from at least one hidden layer to output a result. The number of layers and the number of nodes in each layer may be determined from hyper-parameters of the corresponding neural network model. Such hyper-parameters may be set before or while training the corresponding neural network model on a training dataset. The neural network may correspond to a mathematical function (for example, a sigmoid function or a rectified linear unit) with a set of parameters, tunable during training of the network. The set of parameters may include, for example, a weight parameter, a regularization parameter, and the like. Each node may use the mathematical function to compute an output based on one or more inputs from nodes in other layer(s) (for example, previous layer(s)) of the corresponding neural network model. All or some of the nodes of the each of the set of neural network models may correspond to the same or different mathematical function. In training of the neural network, one or more parameters of each node of the corresponding neural network may be updated based on whether an output of the final layer for a given input (from the training dataset) matches a correct result based on a loss function for the corresponding neural network. The above process may be repeated for the same or a different input until a minima of loss function may be achieved, and a training error may be minimized. Several methods for training are known in art, for example, gradient descent, stochastic gradient descent, batch gradient descent, gradient boost, meta-heuristics, and the like.

Each of the set of neural network may include electronic data, such as a software program, code of the software program, libraries, applications, scripts, or other logic or instructions for execution by a processing device, such as hardware processor. Each of the set of neural network models may include code and routines configured to enable a computing device, such as the system 102, to perform one or more operations. Additionally or alternatively, the neural network may be implemented using hardware including a processor, a microprocessor, a field-programmable gate array (FPGA), or an application-specific integrated circuit (ASIC) to perform or control performance of one or more operations. Alternatively, in some embodiments, each of the neural network model may be implemented using a combination of hardware and software. Although in FIG. 1, the one or more LLMs 106 are shown as integrated within the system 102, the disclosure is not so limited. Accordingly, in some embodiments, the one or more LLMs 106 may be associated with the system 102, without deviation from the scope of the disclosure. In an embodiment, the one or more LLMs 106 may be stored in the server 110.

The user device 108 may include suitable logic, circuitry, interfaces, and/or code that are configured to receive one or more user inputs (for example at least one search query) from the user 114 and transmit the received one or more user inputs to the system 102. The system 102 may be further configured to display the first medical data on the display device 108A associated with the user device 108. Examples of the user device 108 may include, but are not limited to, a computing device, a computer work-station, a smartphone, a cellular phone, a mobile phone, a gaming device, a consumer electronic (CE) device, a mainframe machine, or a server. The display device 108A may comprise suitable logic, circuitry, and interfaces that are configured to display the first medical data. In accordance with an embodiment, the display device 108A may be a touch screen which may enable the user to provide the one or more user inputs via the display device 108A. The touch screen may be at least one of a resistive touch screen, a capacitive touch screen, or a thermal touch screen. The display device 108A may be realized through several known technologies. Examples of such technologies may include, but are not limited to, at least one of a Liquid Crystal Display (LCD) display, a Light Emitting Diode (LED) display, a plasma display, or an Organic LED (OLED) display technology, or other display devices.

The server 110 may include suitable logic, circuitry, and interfaces, and/or code that are configured to store the at least one search query. The server 110 may be further configured to store the one or more MDG databases 104 and the one or more LLMs 106. In some embodiments, the server 110 is configured to train each of the one or more LLMs 106. The server 110 may be implemented as a cloud server and may execute operations through web applications, cloud applications, HTTP requests, database operations, file transfer, and the like. Other example implementations of the server 110 may include, but are not limited to, a database server, a file server, a web server, a media server, an application server, a mainframe server, or a cloud computing server. In at least one embodiment, the server 110 may be implemented as a plurality of distributed cloud-based resources by use of several technologies that are well known to those ordinarily skilled in the art. A person with ordinary skill in the art will understand that the scope of the disclosure may not be limited to the implementation of the server 110 and the system 102 as two separate entities. In certain embodiments, the functionalities of the server 110 can be incorporated in its entirety or at least partially in the system 102, without a departure from the scope of the disclosure.

The communication network 112 may include a communication medium through which the system 102, the one or more MDG databases 104, the one or more LLMs 106, the user device 108, the display device 108A, and the server 110 may communicate with each other. The communication network 112 may be one of a wired connection or a wireless connection. Examples of the communication network 112 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 are configured to connect to the communication network 112 in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

Figure 2:
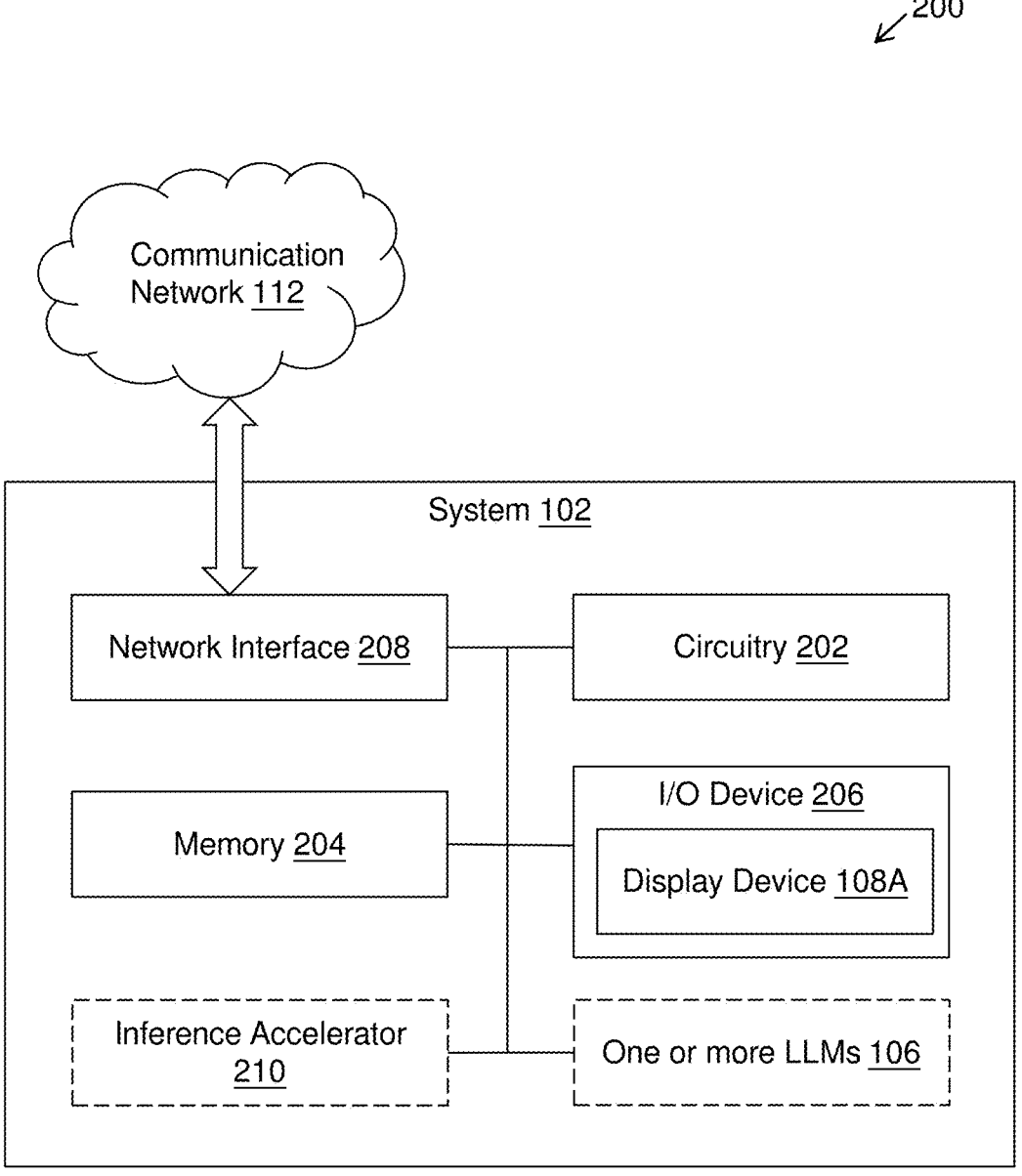
FIG. 2 is a block diagram that illustrates an exemplary system for medical data governance using large language models, in accordance with an embodiment of the disclosure.

FIG. 2 is a block diagram that illustrates an exemplary system for medical data governance using large language models, in accordance with an embodiment of the disclosure. FIG. 2 is explained in conjunction with elements from FIG. 1. With reference to FIG. 2, there is shown a block diagram 200 of the system 102. The system 102 may include a circuitry 202, a memory 204, an input/output (I/O) device 206, a network interface 208, an inference accelerator 210, and the one or more LLMs 106. The circuitry 202 may be communicatively coupled to the memory 204, the I/O device 206, the network interface 208, the inference accelerator 210, and the one or more LLMs 106. The circuitry 202 may include suitable logic, circuitry, and interfaces that are configured to execute program instructions associated with different operations to be executed by the system 102. For example, some of the operations may include, but are not limited to, receiving the user input, applying the one or more LLMs 106, determining metadata, querying the first MDG database 104A, and outputting the retrieved first medical data. The circuitry 202 may include one or more specialized processing units, which may be implemented as an integrated processor or a cluster of processors that perform the functions of the one or more specialized processing units, collectively. The circuitry 202 may be implemented based on a number of processor technologies known in the art. Examples of implementations of the circuitry 202 may be an x86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other computing circuits.

The memory 204 may include suitable logic, circuitry, interfaces, and/or code that are configured to store the program instructions to be executed by the circuitry 202. In at least one embodiment, the memory 204 may store the at least one search query. The memory 204 may also store the one or more LLMs 106. In an embodiment, the memory 204 may be further configured to store first medical data, raw data, and the one or more MDG databases 104. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card. The I/O device 206 may include suitable logic, circuitry, and interfaces that are configured to receive one or more user inputs and provide an output. For example, the system 102 may receive the user input via the I/O device 206. The I/O device 206 may further display the retrieved first medical data. The I/O device 206 which includes various input and output devices, is configured to communicate with the circuitry 202. Examples of the I/O device 206 may include, but are not limited to, a touch screen, a keyboard, a mouse, a joystick, a microphone, a display device, and a speaker.

The network interface 208 may include suitable logic, circuitry, and interfaces that are configured to facilitate a communication between the circuitry 202, the one or more MDG databases 104, the one or more LLMs 106, the user device 108, the display device 108A, and the server 110, via the communication network 112. The network interface 208 may be implemented by use of various known technologies to support wired or wireless communication of the system 102 with the communication network 112. The network interface 208 may include, for example, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry. The network interface 208 is configured to communicate via wireless communication with networks, such as the Internet, an Intranet, or a wireless network, such as a cellular telephone network, a public switched telephonic network (PSTN), a radio access network (RAN), a wireless local area network (LAN), and a metropolitan area network (MAN). The wireless communication may use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VoIP), light fidelity (Li-Fi), Worldwide Interoperability for Microwave Access (Wi-MAX), a protocol for email, instant messaging, and a Short Message Service (SMS).

The inference accelerator 210 may include suitable logic, circuitry, interfaces, and/or code that are configured to operate as a co-processor for the circuitry 202 to accelerate computations associated with the operations of the each of the one or more LLMs 106. The inference accelerator 210 may implement various acceleration techniques, such as parallelization of some or all of the operations of the corresponding one or more LLMs 106. The inference accelerator 210 may be implemented as a software, a hardware, or a combination thereof. Example implementations of the inference accelerator 210 may include, but are not limited to, a GPU, a Tensor Processing Unit (TPU), a neuromorphic chip, a Vision Processing Unit (VPU), a field-programmable gate arrays (FGPA), a Reduced Instruction Set Computing (RISC) processor, an Application-Specific Integrated Circuit (ASIC) processor, a Complex Instruction Set Computing (CISC) processor, a microcontroller, and/or a combination thereof. The functions or operations executed by the system 102, as described in FIG. 2, may be performed by the circuitry 202. Various operations executed by the circuitry 202 are described in detail, for example, in FIGS. 3, 4, and 5.

In operation, the system 102 is configured to receive the user input including at least one search query to retrieve first medical data from one or more MDG databases 104. In an embodiment, the at least one search query is written in a first language. The first language may correspond to any natural language (say English). In an embodiment, the natural language may refer to a way humans may communicate using spoken or written words in everyday conversation(s). The natural language may have its grammar, vocabulary, syntax, and rules for constructing meaningful expressions, allowing individuals to convey complex ideas and emotions. Examples of the natural languages include English, Spanish, Mandarin, and the like. The system 102 may be further configured to apply the one or more LLMs 106 on the received at least one search query. As discussed above, the one or more LLMs 106 may be pre-trained models. In an embodiment, the one or more LLMs 106 may get iteratively trained based on new user requests. The system 102 may be further configured to determine metadata associated with the at least one search query based on the application of the one or more LLMs on the received search query. Based on the determined metadata, the system 102 may be further configured to query the first MDG database 104A of the one or more MDG databases 106. The first MDG database 104A may be queried to retrieve the first medical data. The system 102 may be further configured to output the retrieved first medical data. The output of the retrieved first medical data may correspond to the rendering of the first medical data on the display device 108A associated with the user device 108.

Figure 3:
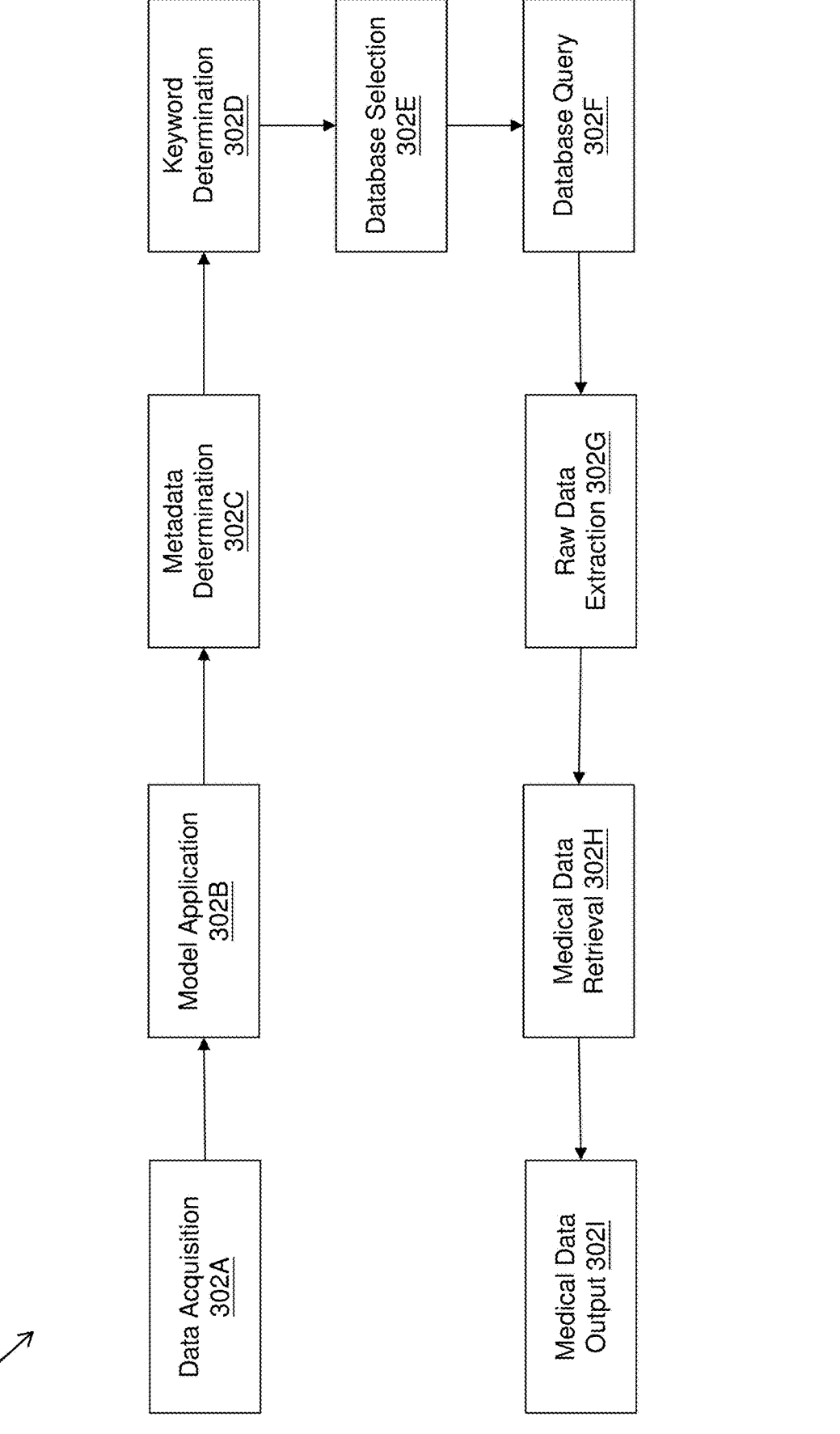
FIG. 3 is a diagram that illustrates exemplary operations for medical data governance using large language models, in accordance with an embodiment of the disclosure.

FIG. 3 is a diagram that illustrates exemplary operations for medical data governance using large language models, in accordance with an embodiment of the disclosure. FIG. 3 is explained in conjunction with elements from FIG. 1 and FIG. 2. With reference to FIG. 3, there is shown a block diagram 300 that illustrates exemplary operations from 302A to 302I, as described herein. The exemplary operations illustrated in the block diagram 300 may start at 302A and may be performed by any computing system, apparatus, or device, such as by the system 102 of FIG. 1 or circuitry 202 of FIG. 2. Although illustrated with discrete blocks, the exemplary operations associated with one or more blocks of the block diagram 300 may be divided into additional blocks, combined into fewer blocks, or eliminated, depending on the particular implementation.

At 302A, a data acquisition operation may be performed. In data acquisition operation, the circuitry 202 is configured to receive the user input from the user 114 of the system 102. The user 114 may be, for example, a doctor, a physician, or any medical professional in a medical environment. In an embodiment, the user 114 may be a patient or any person from the general public. In an embodiment, the input may be received from the user device 108 via the communication network 112 and may include at least one search query that may be written in a first language (say English). As a first example, the at least one search query may be "Find me a patient that most probably has Sepsis." In an embodiment, the at least one search query may be received to retrieve the first medical data from the one or more MDG databases 104. Each MDG database of the one or more MDG databases 104 may include electronic medical records associated with at least one user. The electronic medical records (EMRs) may correspond to digital versions of the paper charts in a healthcare provider's office. Such EMRs may include a patient's medical history, diagnoses, medications, treatment plans, immunization dates, allergies, radiology images, laboratory test results, and the like. In an embodiment, the EMRs may allow for systematic storage, retrieval, and modification of patient data, making it easily accessible to authorized healthcare providers. In an embodiment, the one or more MDG databases 104 may correspond to a specific storage and retrieval tool that can work very efficiently with the one or more LLMs 106 to create an interface and a communication tool for doctors to synthesize responses based on context and clarity.

In an embodiment, the EMRs may include medical history reports, physical examination reports, diagnostic reports, progress notes, consultation reports, operative reports, discharge summaries, medication reports, billing reports, and insurance reports. Examples of the EMRs may correspond to at least one of doctor consultation notes, doctor progress notes, nurses' notes, a prescription history, problem lists, International Classification of Diseases (ICD) codes, laboratory results, pathology reports, X-radiation (X-RAY) reports, computed tomography (CT) reports, magnetic resonance imaging (MRI) reports, ultrasound reports, cardiac catheter reports, or cardiac stress reports associated with at least one user. In another embodiment, the one or more MDG databases 104 may further include records associated with multiple patients, medical facilities, and medical procedures. The medical facilities encompass diverse settings designed to provide healthcare services and support to individuals. The medical facilities may include, but are not limited to, hospitals, clinics, urgent care centers, rehabilitation centers, and nursing homes. The medical procedures may encompass a vast range of interventions performed by healthcare professionals to diagnose, treat, or prevent various health conditions. Such medical procedures may include diagnostic procedures (such as X-rays, CT scans, MRI scans, ultrasounds, and PET scans), surgical procedures (such as laparoscopy, and arthroscopy), therapeutic procedures (such as chemotherapy, and radiation therapy), cardiovascular procedures (such as angioplasty, coronary artery bypass grafting (CABG)), obstetric and gynecological procedures (such as cesarean section, colposcopy), orthopedic procedures (such as joint replacement, fracture repair), and dental procedures (such as fillings and root canals, and extractions).

At 302B, a model application operation may be executed. In the model application operation, the circuitry 202 is configured to apply the one or more LLMs 106 on the received at least one search query. The one or more LLMs 106 translate natural-language queries (e.g., conversational phrases like 'Find sepsis patients') into structured metadata, eliminating rigid syntax requirements while maintaining contextual accuracy. As discussed above, each of the one or more LLMs 106 may be pre-trained models that may be trained to extract metadata based on the received at least one search query. In an embodiment, the one or more LLMs 106 may have been trained on all medical textbooks that may be known in the art. As an example, the one or more LLMs 106 may put together about 65 billion words and may be used to provide all metadata needed for successful research and then provide it back as an interface to humans. Specifically, the one or more LLMs 106 may be used as an interface for the research.

At 302C, a metadata determination operation may be executed. In the metadata determination operation, the circuitry 202 is configured to determine metadata associated with the at least one search query. In an embodiment, the metadata may be determined based on the application of the one or more LLMs 106 on the received search query. The metadata may correspond to information about the data, such as the type of data, the date it was collected, and the patient it is associated with. By indexing the metadata, users (such as doctors) may be able to search for data across MDG databases without having to access the data itself. In an embodiment, the metadata may be required for successful research. Specifically, the one or more LLMs 106 may be used to provide all metadata that are needed for successful research and provide it back as an interface to the user 114. With reference to the first example, the one or more LLMs 106 by itself may find the metadata needed to define sepsis.

At 302D, a keyword determination operation may be executed. In the keyword determination operation, the circuitry 202 is configured to determine at least one keyword from the determined metadata. In an embodiment, the least one keyword is associated with the at least one search query. In an embodiment, the at least one keyword corresponds to one of a name of a user, a name of a medical facility, a name of a disease, or a name of a medical procedure. In an embodiment, the system 102 is configured to apply the one or more LLMs on the determined metadata to further determine the at least one keyword. In another embodiment, the system 102 is configured to apply a natural language processing (NLP) model on the metadata to determine the at least one keyword. With reference to the first example, the at least one keyword may be "Sepsis".

At 302E, a database selection operation may be executed. In the database selection operation, the circuitry 202 is configured to select first MDG database 104A of the one or more MDG databases 104 based on the determined at least one keyword. In an embodiment, each of the one or more MDG databases 104 may be associated with at least one keyword. For example, the first MDG database 104A may include all the information about the patients associated with at least one medical disease (such as sepsis), second MDG database 104B may include medical records associated with the set of patients in a geographic area (such as a city or a town), third MDG database 104C may include details about all the patients, medical equipment, facilities available in at least one medical clinic in the geographic area, and so on.

At 302F, a database query operation may be executed. In the database query operation, the circuitry 202 is configured to query the selected first MDG database 104A of the one or more MDG databases 104. In an embodiment, querying the first medical database 104A may refer to a process of requesting specific information or data from the first medical database 104A. The system 102 is configured to query at least the first MDG database 104A of the one or more MDG databases 104 to retrieve the first medical data associated with the at least one search query.

At 302G, a raw data extraction operation may be executed. In the raw data retrieval operation, the circuitry 202 is configured to extract, from the first MDG database 104A, raw data associated with the determined metadata based on the querying the first MDG database 104A. The raw data may include all the data extracted from the first MDG database 104A that may be associated with the determined at least one keyword. With reference to the first example, the raw data may include a knowledge base associated with the medical disease sepsis, details associated with one or more patients suffering from sepsis in the geographical area, medical facilities offering treatment for sepsis, trends in the people suffering from sepsis, and the like.

At 302H, a medical data retrieval operation may be performed. In the medical data retrieval operation, the circuitry 202 is configured to retrieve the first medical data. In an embodiment, the system 102 is configured to retrieve the first medical data from the extracted raw data. To determine the first medical data, the system 102 is configured to generate one or more constructs associated with the one or more LLMs to be applied on the extracted raw data. The one or more constructs may be associated with the determined metadata. The system 102 may be further configured to retrieve the first medical data based on the application of the generated one or more constructs on the extracted raw data. The first medical data may correspond to an appropriate answer to the at least one search query and may be a desired answer to the at least one search query. With reference to the first example, the first medical data may correspond to details associated with one or more patients suffering from sepsis in the geographical area. The details may include a name, an age, a sex, an address, a medical history, and the like associated with the one or more patients suffering from the medical disease sepsis.

At 302I, a medical data output operation may be performed. In the medical data output operation, the circuitry 202 is configured to output the retrieved first medical data. In an embodiment, the output of the retrieved first medical data may correspond to displaying the first medical data on the user device 114. In another embodiment, the output of the first medical data may correspond to storing the first medical data in the one or more MDG databases 104.

In an embodiment, the disclosed system is configured to create thousands of descriptions (permutations of data elements) results using metadata from an LLM Query, from the first medical data governance database. This structured data, associated with the determined metadata, may be expressed as a configuration to LLM in the form of specific language terms and sentences used to train the LLM (English or German, for example). The LLM query may further create a specific syntax for medical data governance, based on the context of the question and previous queries. In accordance with an embodiment, the system may extract, from the first medical data governance database, raw structured data associated with the determined metadata based on querying the first medical data governance database. The system then, based on the query metadata and the raw data, constructs one or more LLM configurations that may be specific to metadata and raw data to be further apply the one or more LLMs. The system may further retrieve the first medical data based on the application of the one or more LLMs on the extracted raw data. The system may further output the retrieved first medical data.

Figure 4:
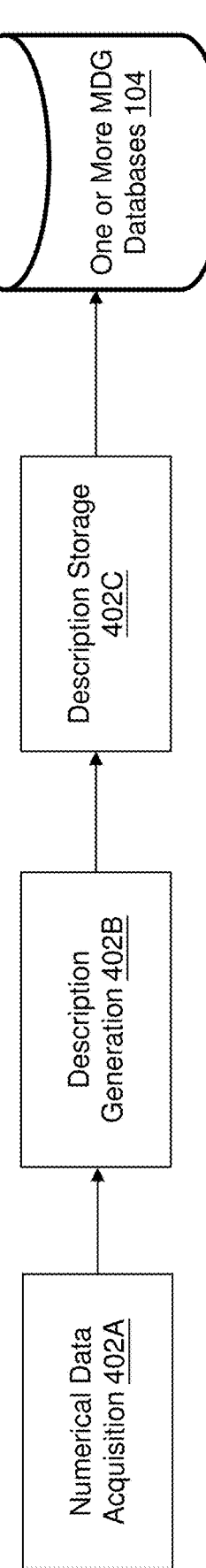
FIG. 4 is a diagram that illustrates exemplary operations for the generation of description associated with numerical data, in accordance with an embodiment of the disclosure.

FIG. 4 is a diagram that illustrates exemplary operations for the generation of description associated with numerical data, in accordance with an embodiment of the disclosure. FIG. 4 is explained in conjunction with elements from FIG. 1, FIG. 2, and FIG. 3. With reference to FIG. 4, there is shown a block diagram 400 that illustrates exemplary operations from 402A to 402C, as described herein. These operations showcase another capability of the system. The exemplary operations illustrated in the block diagram 400 may start at 402A and may be performed by any computing system, apparatus, or device, such as by the system 102 of FIG. 1 or circuitry 202 of FIG. 2. Although illustrated with discrete blocks, the exemplary operations associated with one or more blocks of the block diagram 400 may be divided into additional blocks, combined into fewer blocks, or eliminated, depending on the particular implementation.

At 402A, a numerical data acquisition operation may be performed. In the numerical data acquisition operation, the system 102 is configured to acquire numerical data. The numerical data may refer to information that may be quantifiable and expressed in numerical form. In an embodiment, the numerical data may be captured by one or more medical devices that may be associated with the at least one user. Each of the one or more medical devices may correspond to instruments, tools, machines, implants, software, or any similar item used for medical purposes, including diagnosis, treatment, monitoring, or prevention of diseases or other health conditions. Examples of the one or more medical devices may include a blood glucose meter, a blood pressure meter, an electrocardiogram (ECG) Monitor, a pulse oximeter, and the like. As a second example, the acquired numerical data may be of "Blood Pressure: 82 bpm" or "Blood Oxygen: 98%".

At 402B, a description generation operation may be performed. In the description generation operation, the system 102 is configured to generate a description associated with the received numerical data. The description may be written in the first language and may involve summarizing and presenting the essential characteristics, patterns, and properties of the acquired numerical data. In an embodiment, the system 102 is configured to generate descriptions of all numerical data including time segments, variability, range, distribution, and statistical calculations used in medical papers, publications, and medical documentation related to specific patient conditions. In an embodiment, the system 102 is configured to apply the NLP model to the acquired numerical data. Based on the application of the NLP model, the system 102 is configured to generate the description of the acquired numerical data. With reference to the second example, the generated description of the numerical data "Blood Pressure: 82 bpm" may be "The blood pressure of the user may be eighty-two beats per minute".

At 402C, a description storage operation may be performed. In the description storage operation, the system 102 is configured to store the generated description in at least one of the one or more MDG databases 104. The stored description may be used for medical data retrieval as discussed in the FIG. 3.

Figure 5:
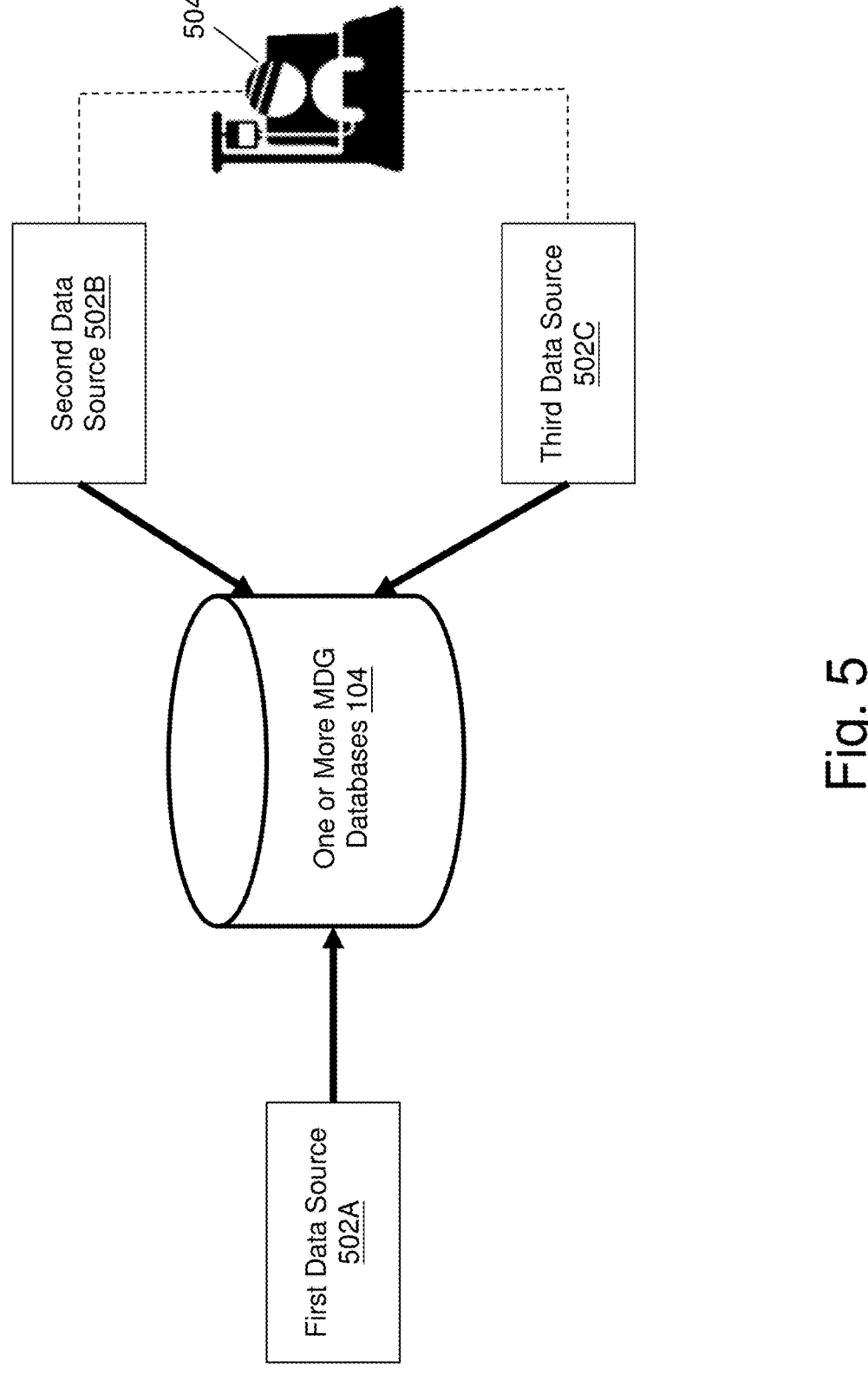
FIG. 5 is a diagram that illustrates a set of data sources for obtaining medical data to be stored in one or more medical data governance databases, in accordance with an embodiment of the disclosure.

FIG. 5 is a diagram that illustrates a set of data sources for obtaining medical data to be stored in one or more medical data governance databases, in accordance with an embodiment of the disclosure. FIG. 5 is explained in conjunction with elements from FIGS. 1, 2, 3, and 4. With reference to FIG. 5, there is shown a diagram 500 that includes a set of data sources 502 for obtaining medical data to be stored in the one or more MDG databases 104. In an embodiment, the set of data sources 502 may include, but is not limited to, a first data source 502A, a second data source 502B, and a third data source 502C.

In an embodiment, the first data source 502A may correspond to legacy medical knowledge. Specifically, the legacy medical knowledge refers to traditional or historical medical practices, theories, and information that have been passed down through generations and may encompass the methods, beliefs, and treatments used in medicine. In an embodiment, the legacy medical knowledge may include textbooks associated with the medical field, research papers associated with the medical field, patents associated with the medical field, publications associated with the medical field, clinical trials, and research databases, healthcare guidelines, and protocols, medical conferences and symposia, drug databases and formularies, public health reports and epidemiological data, and the like.

In an embodiment, the second data source 502B and the third data source 502C may be associated with at least one patient 504 (of multiple patients). The second data source 502B may correspond to medical data that may be obtained from the one or more medical devices (or equipment) that may be associated with the patient 504 to capture corresponding parameters associated with the patient 504. For example, a smart watch associated with (or worn by) the patient 504 may capture the heart rate of the patient 504 and may further store the captured heart rate of the patient 504 in the one or more MDG databases 104. In some embodiments, the data obtained from the one or more medical devices may include numerical data. In such instances, the system 102 is configured to obtain the numerical data captured by one or more medical devices associated with the patient 504. The system 102 is configured to generate a description associated with the received numerical data and further store the generated description in at least one of the one or more MDG databases 104. Details about the generation of the description are provided, for example, in FIG. 4.

In an embodiment, the third data source 502C may be associated with a patient 504 (of multiple patients) and may correspond to medical data that may be obtained from medical records of the patient 504. Such records may include, but are not limited to, doctor consultation notes, doctor progress notes, nurses' notes, a prescription history, problem lists, International Classification of Diseases (ICD) codes, laboratory results, pathology reports, X-radiation (X-RAY) reports, computed tomography (CT) reports, magnetic resonance imaging (MRI) reports, ultrasound reports, cardiac catheter reports, or cardiac stress reports associated with the patient 504. In an embodiment, the data generated or stored in the one or more MDG databases 104 may be utilized by the system 102 to train the one or more LLMs 106 to increase the performance of the one or more LLMs 106.

Figure 6:
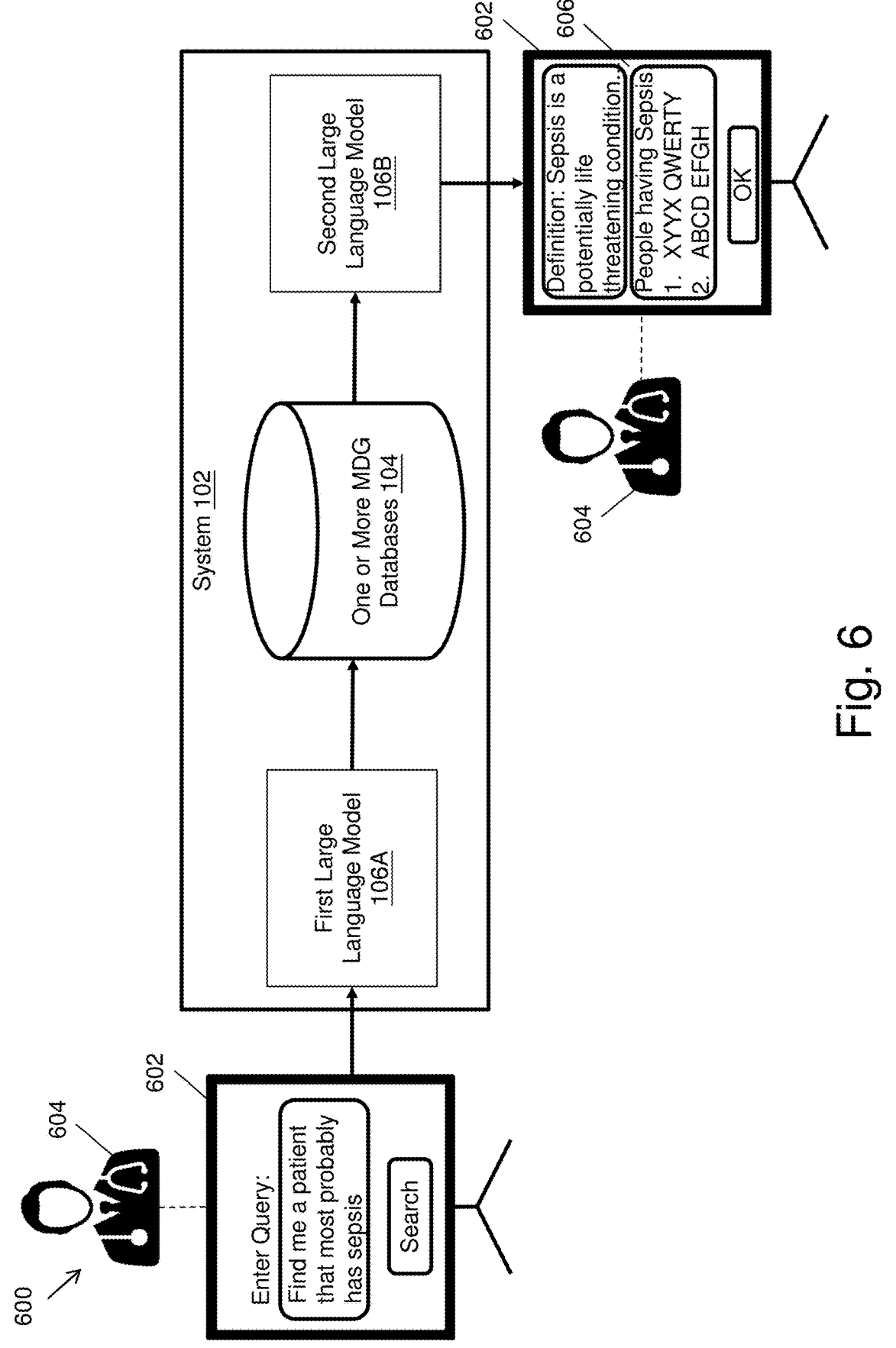
FIG. 6 is a diagram that illustrates an exemplary scenario for an application for medical data governance using large language models, in accordance with an embodiment of the disclosure.

To further illustrate the utility of the system, FIG. 6 is a diagram that illustrates an exemplary scenario for an application for medical data governance using large language models, in accordance with an embodiment of the disclosure. FIG. 6 is explained in conjunction with elements from FIGS. 1, 2, 3, 4, and 5. With reference to FIG. 6, there is shown an exemplary scenario 600. There is further shown an electronic device 602 associated with a user 604 who may be a medical professional (for example, a doctor (physician), a nurse, a surgeon, a pharmacist, a dentist, a therapist, and the like). In an embodiment, the user 604 may wish to determine information related to medical field or related to a patient (say the patient 504) whom the user 604 may be treating. The user 604 may enter a query related to medical field or related to a patient (say the patient 504) whom the user 604 may be treating on the electronic device 602. Based on the reception of the query, the electronic device 602 may transmit the query to the system 102 via the communication network 112. By way of a first example and not limitation, the query may be "Find me a patient that most probably has sepsis".

Based on the reception of the query from the electronic device 602, the system 102 is configured to apply the one or more large language models (LLMs) 106 on the received at least one search query. Based on the application of the one or more LLMs 106, the system 102 may determine metadata associated with the at least one search query. The one or more LLMs may be pre-trained to determine metadata associated with the search query. With reference to the first example, the one or more LLMs may find what is the metadata needed to define sepsis. The system 102 may be further configured to query the first MDG 104A of the one or more MDG databases 104 based on the determined metadata to retrieve medical data. The medical data may be associated with the search query and may include at least one person who most probably has sepsis. In an embodiment, the system 102 is configured to extract raw data associated with the determined metadata from the first MDG database 104A. System 102 may be further configured to apply the one or more LLMs 106 on the extracted raw data. Specifically, the system 102 is configured to apply the second LLM 106B of the one or more LLMs 106 on the extracted raw data. Based on the application of the one or more LLMs 106 on the extracted raw data, the system 102 is configured to retrieve the first medical data. The retrieved first medical data may correspond to an answer to the query and may include details about at least one patient who might have sepsis. The system 102 may be further configured to transmit the retrieved first medical data to the electronic device 602. The electronic device 602 may receive the first medical data and render the first medical data on a user interface (UI) of the user device 606.

In another embodiment, the user 604 may use the system 102 to query information related to the patient 504. For example, the user 604 may use the system 102 to determine whether the patient 504 may have a particular medical condition (say sepsis). In such an embodiment, the system 102 may query the one or more MDG databases 104 that may include information associated with a medical history of the patient. The system 102 may further apply the one or more LLMs on the medical history of the patient and generate a response indicating whether the patient may have a particular medical condition (say sepsis).

In another embodiment, the system 102 is configured to receive real-time medical data associated with at least one user from one or more medical devices associated with (say worn by) the patient 504. Based on the received real-time medical data and the one or more MDG databases, the system 102 is configured to determine at least one upcoming event associated with a medical condition of the patient 504. The system 102 may be further configured to output the determined at least one upcoming event on the electronic device 602. In another embodiment, the system 102 may trigger audible or visual notifications indicating the at least one upcoming event. By way of example and not limitation, the system 102 may transmit notifications to user devices (or electronic device 602) (such as smartphones or computer(s)) associated with the user 604 or the patient 504. By way of example and not limitation, the system 102 may receive real-time data associated with the blood pressure of the patient 504 from a smartwatch worn by the patient 504. The received real-time data may indicate an increase in the blood pressure of the patient 504 over a short time period. Based on the received real-time data, and the one or more MDG databases 104 that may include information from legacy medical knowledge, such an increase in blood pressure in a certain time period may be indicative of an upcoming blood pressure attack (or hypertensive crisis). The system 102 may output the determined upcoming blood pressure attack (or hypertensive crisis) on the user device 104. Based on the output of the upcoming blood pressure attack, the user 604 may provide medications to the patient 504 to overcome (or at least to reduce the impact of) the upcoming blood pressure attack. Therefore, the disclosed system 102 may save the lives of the patients automatically without any human intervention.

In another embodiment, the system 102 (or the MDG system) may enable federated search of medical data. The federated search may allow users to search for data across multiple distributed systems without having to centralize the data in one location. This may be important for protecting the privacy of patients and for reducing the administrative burden on hospitals. There may be several different approaches to the federated search of medical data. One important approach of MDG is to generate metadata to index the sensitive data. As discussed above, the metadata is information about the data, such as the type of data, the date it was collected, and the patient it is associated with. By indexing the metadata, the users may be able to search for data across multiple systems without having to access the data itself. Another advantage of the MDG may be that it acts as a centralized storage system for different healthcare systems or medical facilities (such as hospitals) that may be accessed using a query mediator. The query mediator (or the one or more LLMs) may be a component that may acts as an intermediary between the user and the distributed MDG subsystems. The query mediator component receives the user's search query and forwards it to the relevant MDG subsystems, providing unifying results back to the user.

Some specific examples of how federated search of medical data is used may include a researcher searching for data on patients with a particular disease across multiple hospitals. This could help the researcher to identify new risk factors for the disease or to develop new treatments. Another example may be that a clinician may search for data on patients who have had a particular surgery across multiple hospitals. This could help the clinician to learn from the experiences of other surgeons and to improve their surgical outcomes. Another example may be that a patient may search for data on his/her medical history across multiple hospitals. This could help the patient to better understand their health and to make informed decisions about their care. Therefore, MDG federated search of medical data may be a powerful tool that may be used to improve patient care and to advance medical research. MDG may be essential for enabling federated search in a secure and privacy-preserving manner.

In addition to these general benefits, MDG can also provide a number of specific benefits for research, such as facilitating data sharing, supporting the development of new research methods, and promoting the translation of research findings into clinical practice. Specifically, MDG may facilitate data sharing between researchers, which can help to accelerate research and improve the quality and impact of research findings. MDG may also support the development of new research methods, such as the use of machine learning and artificial intelligence to analyze large datasets. Furthermore, MDG may also help to promote the translation of research findings into clinical practice by ensuring that data is collected and stored in a way that is compatible with clinical systems. The specific value of MDG for research on patient medical data is that it may allow researchers to access and use large datasets of patient data without compromising the privacy of individual patients. This is possible because MDG may ensure that data is de-identified before it is used for research. Such de-identified patient medical data may be used to conduct a wide range of research studies, including clinical trials, Observational studies, and Basic science research. Therefore, MDG may be essential for ensuring that medical data is used responsibly and ethically for research. This is important for protecting the privacy of patients, ensuring the quality of data, promoting the ethical use of data, and accelerating the development of new medical treatments and cures.

Figure 7:
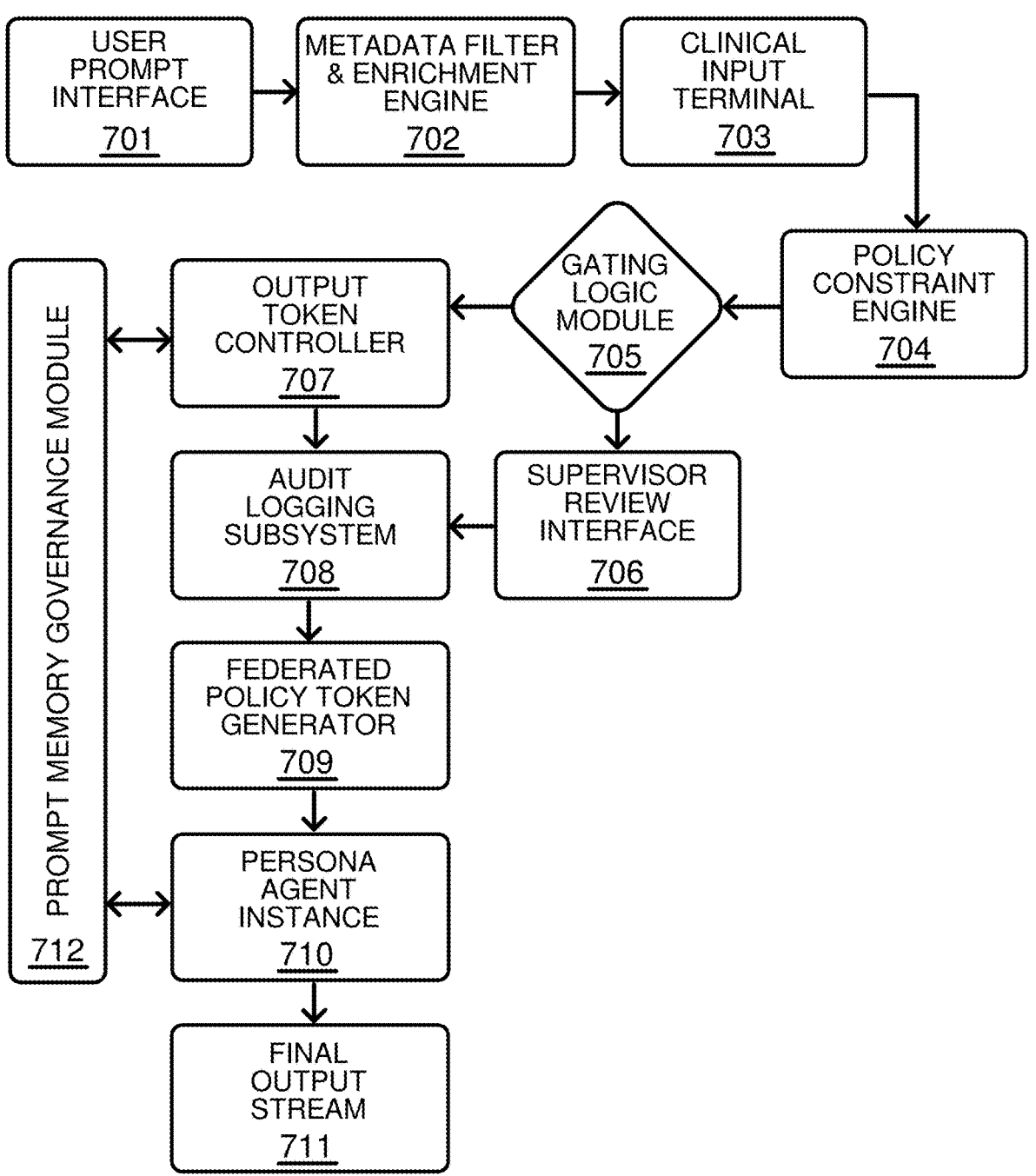
FIG. 7 is a block diagram depicting a persona-agent governance pipeline that captures enriched metadata, enforces policy, invokes supervisory gating and appends cryptographically signed audit records.

The underlying architecture that enables these capabilities is now described in greater detail with reference to FIGS. 7-12. As shown in FIG. 7, a prompt first reaches the User-Prompt Interface 701, where it is accepted from any initiator. An initiator could be a human user, artificial intelligence agent, or automated system or workflow responsible for generating a prompt and initiating a persona agent session. The Metadata Filter & Enrichment Engine 702 immediately enriches the prompt by attaching metadata to the received prompt. The metadata may include: credential information, institutional affiliation, geographic location, LLM-instance accreditation, privacy flags, risk class, policy context and the entire delegation chain. The enriched prompt flows to the Persona Role Constructor 703 in FIG. 7, which launches an agent on a nearby computing node such as Edge Device A 1101 shown in FIG. 11, selecting an appropriately sized localized persona-agent model to fit device constraints that refer to the practical limits (such as that of computational, memory and storage, power/battery, latency, bandwidth, and security/regulatory) of the particular computing node on which the persona agent will run.

Figure 9:
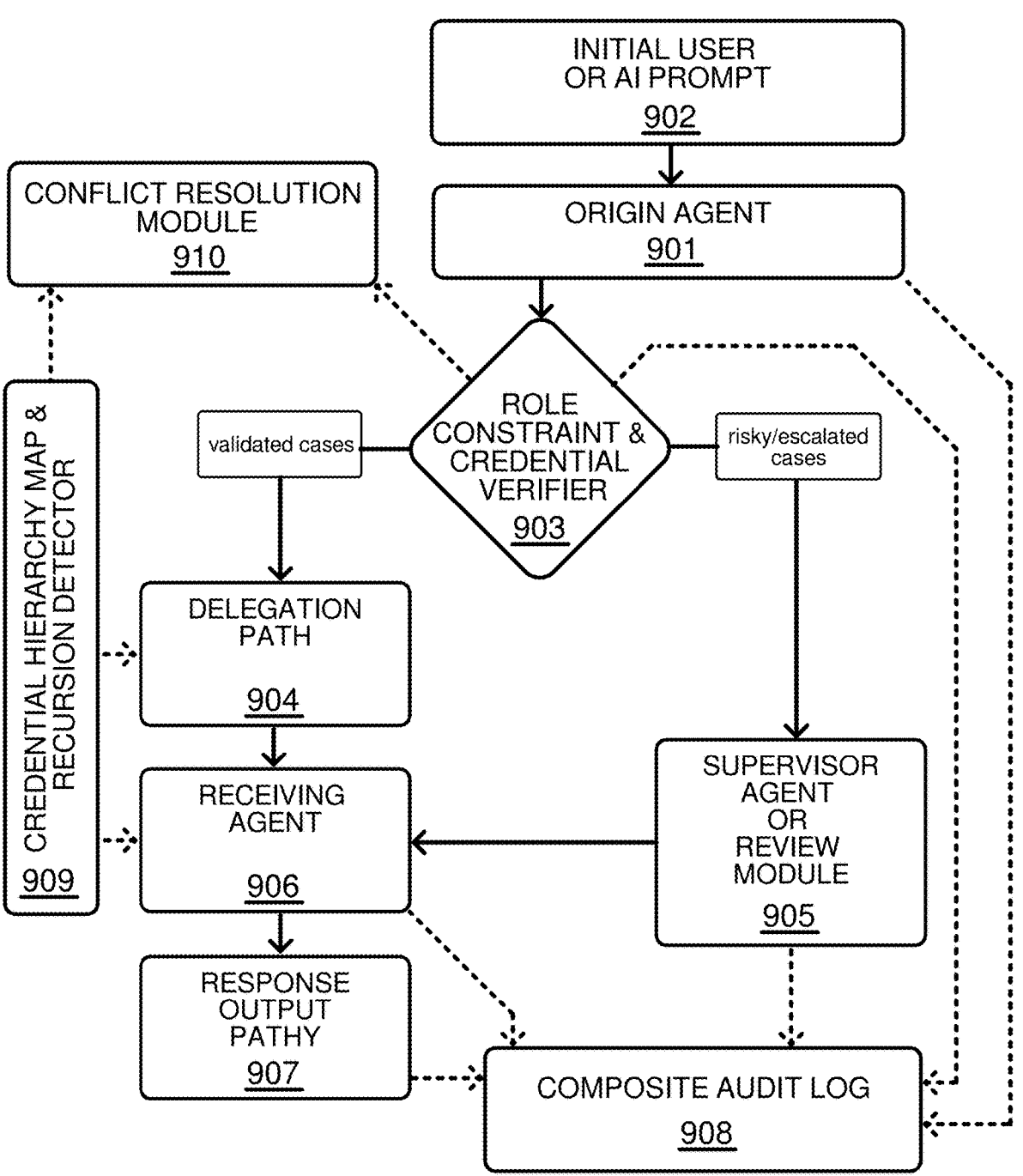
FIG. 9 is a graph diagram showing inter-agent delegation with credential-hierarchy enforcement and recursion detection to prevent unauthorized or cyclical hand-offs.

The newly created agent is then scrutinized by the Policy Constraint Engine 704 of FIG. 7—mirrored as Policy Engine 1204 in FIG. 12—which dynamically checks every contemplated action (produced by the persona agent) against institutional, regulatory (including HIPAA, GDPR, and EU AI Act), and jurisdictional policy constraints by consulting a Credential Hierarchy Map and Recursion Detector 909 in FIG. 9. Policy Engine is basically a module, process, or component configured to evaluate agent actions, session context, and metadata against defined policy constraints, including institutional, regulatory, jurisdictional, or risk-based policies. To simply put, policy constraint is a rule, requirement, or logical condition, defined by institutional or regulatory authority, that limits or governs the actions, outputs, or operational context of a persona agent. Credential Hierarchy Map is a logical model or data structure defining the permissible paths, authority boundaries, and escalation protocols for delegation and credential inheritance within a given institution or network. Recursion Detector is a module or process that analyzes the delegation chain or credential hierarchy to detect and prevent unauthorized, cyclical, or recursive delegation events. Should the policy check raise a risk flag, the Gating Logic Module 705 in FIG. 7 freezes execution and invokes the Supervisor Review Interface 706 (also element 905 in FIG. 9). A credentialled human or digital supervisor may approve, modify or reject the pending action, and the result is immutably recorded by the Audit Logging Subsystem 708 in FIG. 7 and the Local Audit Ledger 1106 in FIG. 11, forming a tamper-evident, cryptographically chained log within mesh-network-wide distributed ledger which is a synchronized, tamper-evident record of audit events, policy decisions, delegation changes, and failover events maintained across multiple edge devices and mesh nodes, supporting regulatory and forensic traceability. The mesh-network-wide distributed ledger is the aggregate, peer-replicated, cryptographically linked audit record formed by the union of all local audit ledgers maintained on individual computing nodes.

Figure 8:
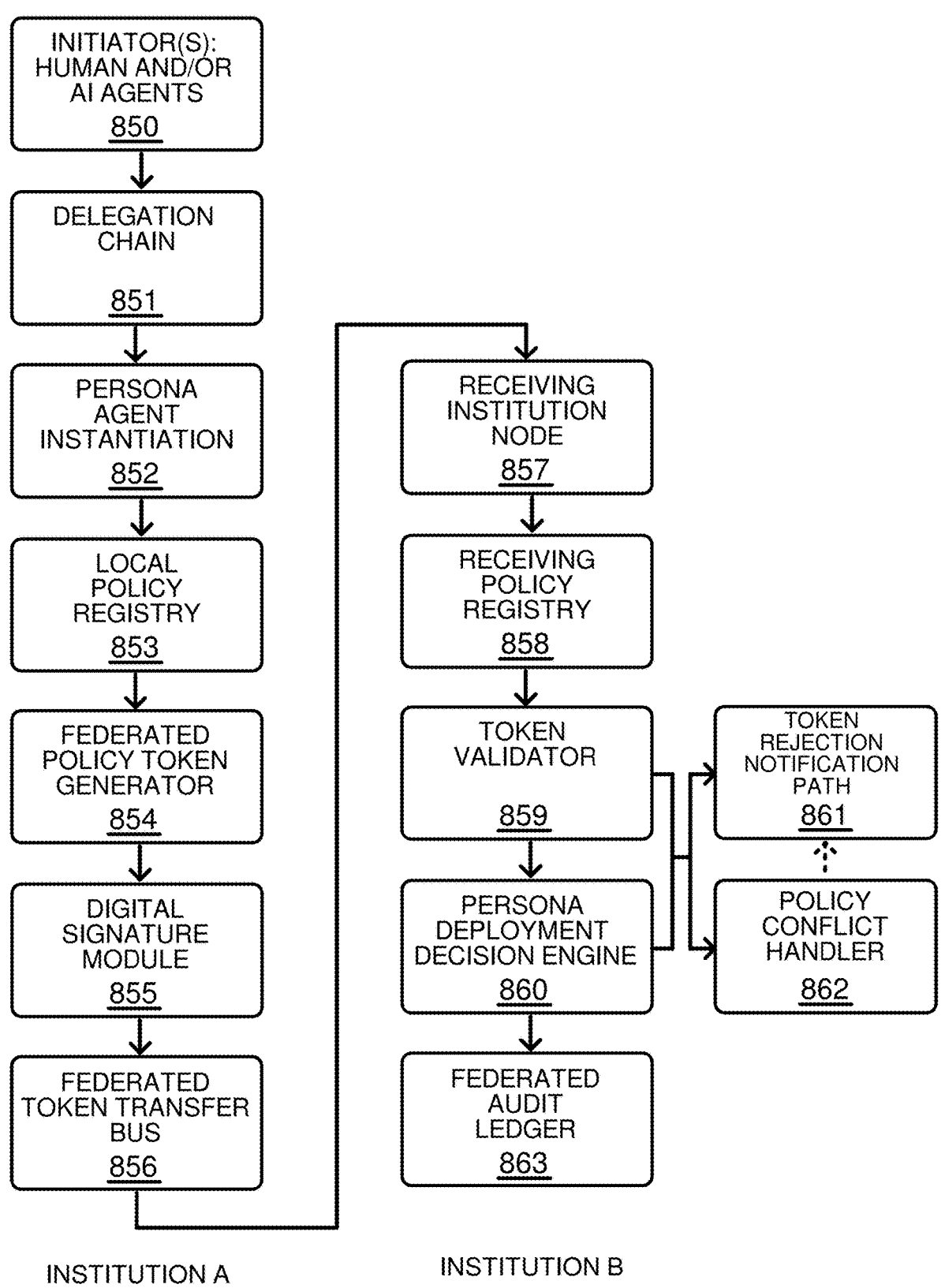
FIG. 8 illustrates a prompt-passport lifecycle and federated compliance-token flow enabling secure cross-institutional validation of delegation chains, credentials and policy context.

Outputs that clear gating pass through the Output Token Controller 707 in FIG. 7 and—when a workflow crosses institutional boundaries—enter the Federated Policy-Token Generator 709. FIG. 8 traces this pathway: Generator 709 encapsulates delegation chain 851, credential lineage and policy snapshot into a signed compliance token 854. The Digital-Signature Module 855 seals the token before it traverses the Federated Token-Transfer Bus 856 to a Receiving Institution Node 857. Thereafter, the Token Validator 859 compares the packet with the Receiving Policy Registry 858. If all checks pass, the Persona-Deployment Decision Engine 860 instantiates a compliant agent, and if the validation fails, the Token-Rejection Notification Path 861 and Policy-Conflict Handler 862 abort deployment, transmit a signed rejection notice to the originator detailing the policy conflict, and record the entire incident—including token details and denial reason—in the Federated Audit Ledger 863 for forensic and regulatory review. The Receiving Policy Registry 858 is the destination institution's authoritative store of policy artefacts. The registry therefore acts as both a reference baseline for compliance checks and a version-tracking system that lets the institution prove which policy set was in force at the moment of validation.

While an agent session is live, the Prompt-Memory Governance Module 712 in FIG. 7 enforces a session-memory window. A session-memory window is a defined range of context, history, or duration within which a persona agent may retain prompt, user, or workflow information. The window is governed by policy or privacy rules and is subject to expiration, reset, or truncation. Expirations, resets or truncations—logged as Token-Memory-Window-Expiration 1007 in FIG. 10—join other lifecycle events: Agent-Instantiation 1001, Metadata-Enrichment 1002, Policy-Compliance Check 1003, Supervisor-Gate Trigger 1004, Approved-Output 1005, policy-version mismatch 1009 and credential-revocation signal 1010. Each is hashed and chained, ensuring a complete forensic trail.

Figure 11:
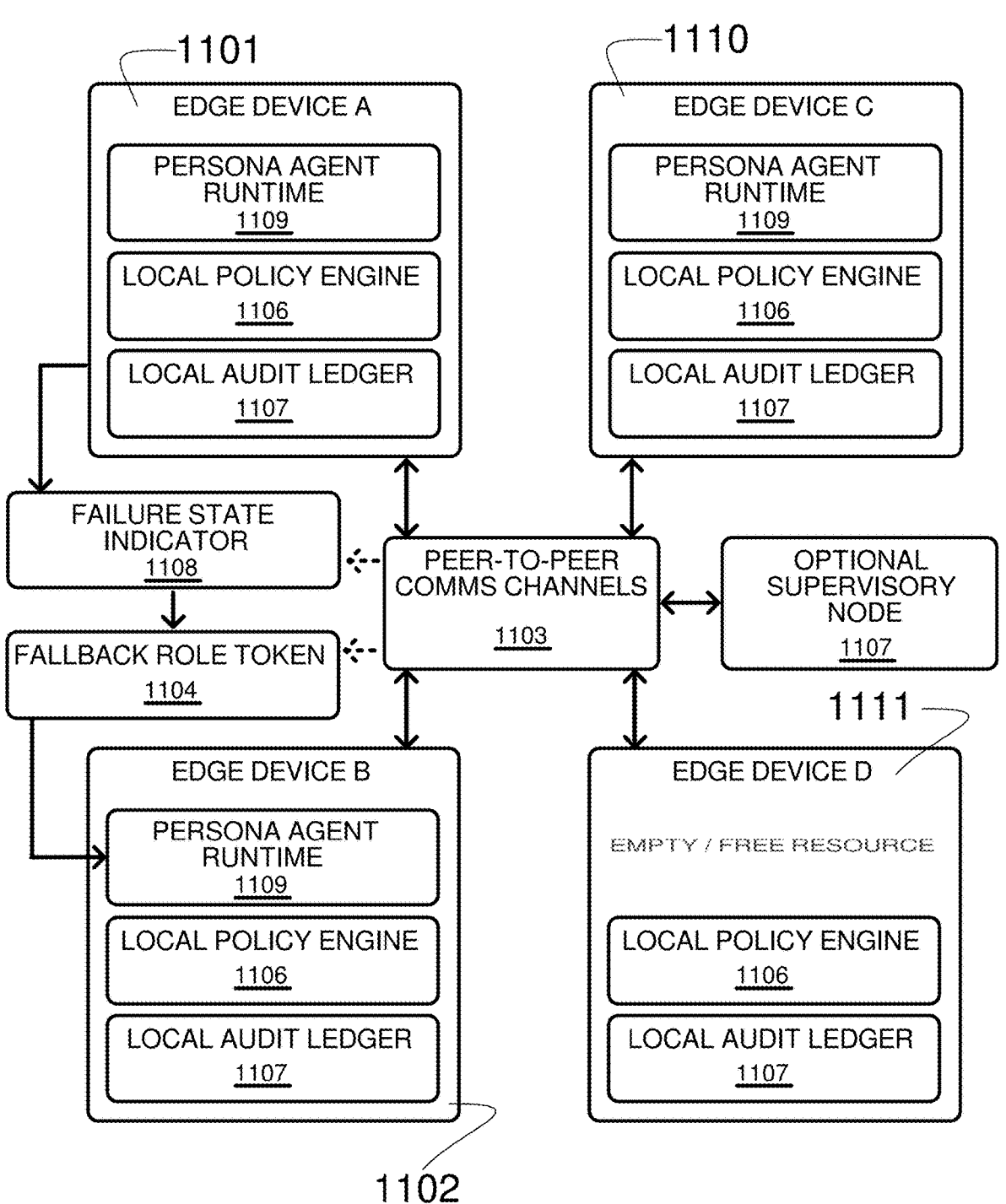
FIG. 11 shows a decentralized mesh network of edge devices with peer-to-peer communication, fallback control modules and role-switch tokens for automatic fail-over and workload balancing.

As shown in FIG. 11, edge devices (e.g., 1101, 1102) operate autonomously during network partitions. A resident Fallback Control Module issues a cryptographically signed Fallback Role Token 1104 to standby Edge Device B 1102 when Failure-State Indicator 1108 detects faults, ensuring uninterrupted governance and audit integrity without centralized dependency. A Fallback Control Module refers to a component or module configured to monitor device availability and operational health, and to coordinate automatic transfer of operational context, session memory, and delegation state to a pre-authorized peer device upon detection of device failure or unavailability. Edge devices collaborate inside the peer-to-peer mesh shown in FIG. 11, exchanging messages over the Comms Channel 1103. Because each node hosts its own Local Policy Engine 1105 and ledger 1106 and can operate in an offline mode, governance, memory limits and audit integrity persist throughout network partitions. In the offline mode, a computing node continues persona agent operation, policy enforcement, and audit logging in the absence of network connectivity, with data synchronization performed upon reconnection. Once connectivity returns, local chains are reconciled by consensus—optionally overseen by a Supervisory Node 1107. A supervisory node is an optional node within the mesh network, configured to receive status updates from edge devices and coordinate mesh topology adjustments or high-level monitoring. A mesh network is a decentralized, peer-to-peer network architecture comprising multiple computing nodes ("mesh nodes") which communicate directly, coordinate roles, share audit data, support failover, and synchronize operational context.

Delegation between agents follows the pathway in FIG. 9. An Origin Agent 901 receives an Initial Prompt 902, hands it off along Delegation Path 904 to a Receiving Agent 906, and returns results via the Response-Output Path 907—provided the Role-Constraint & Credential Verifier 903 and recursion detector 909 authorize the exchange. Every event feeds the Composite Audit Log 908, and anomalies route to the Conflict-Resolution Module 910. Throughout this pipeline, each inbound datum is secured by an input chain-of-trust; its signature remains bound to every downstream decision and digital artifact produced by the Artifact Generator 1209, while utilisation records settle in the Asset Registry & Billing Engine 1210, closing the compliance loop defined in FIG. 12. An input chain-of-trust is a process and data structure whereby every data input, prior to use by a persona agent, is cryptographically timestamped, source-verified, and semantically labeled, with this provenance record persistently and immutably linked to all downstream agent actions, outputs, artifacts, and registry or audit events.

Figure 10:
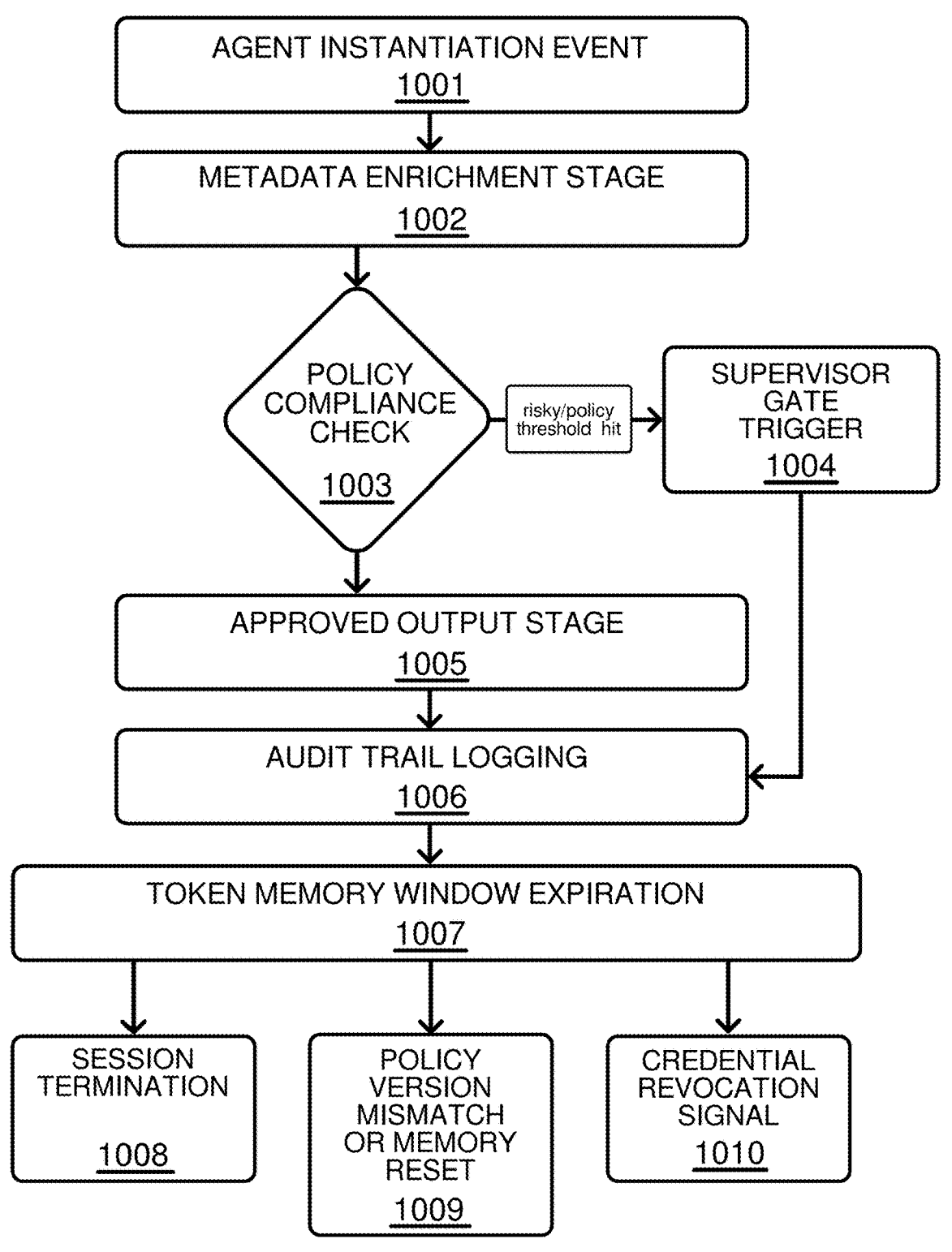
FIG. 10 is a flow diagram of a persona-agent session lifecycle, including instantiation, policy evaluation, supervisory gating, audit logging, memory-window expiration, credential revocation and session termination.

In summary, by weaving together the runtime pipeline of FIG. 7, the federated passport flow of FIG. 8, the delegation logic of FIG. 9, the lifecycle chronology of FIG. 10, the self-healing mesh of FIG. 11 and the system-level overview of FIG. 12, the invention delivers prompt-driven agent instantiation, fine-grained metadata capture, real-time policy enforcement, gated supervision, session-memory governance, resilient mesh deployment, peer-to-peer fail-over and federated compliance—while preserving an immutable, end-to-end audit trail for any compliance-sensitive domain. By unifying prompt-driven agent instantiation, dynamic metadata capture, real-time policy enforcement, supervisor gating, session-memory governance, distributed audit, peer-to-peer fail-over and federated compliance tokens within a self-healing mesh of computing nodes, the invention supplies a comprehensive governance fabric for AI in regulated domains. Each agent action is contextualized by credential and policy lineage; decision-making continues uninterrupted during outages; and every datum—from initial input to final output—remains verifiable in an immutable audit chain. Although the preferred embodiments focus on healthcare, the modular design extends readily to finance, logistics, industrial automation or any setting where decentralised AI must act under stringent, auditable constraints. All variations employing the disclosed mechanisms for policy-constrained agent governance therefore fall within the spirit and scope of the invention.

Various embodiments of the disclosure comprise the system 102 for medical data governance using large language models. The system 102 may comprise, for example, the circuitry 202, the memory 204, the I/O device 206, and the network interface 208, and/or the inference accelerator 210. The circuitry 202 of the system 102 is configured to receive the user input including at least one search query to retrieve first medical data from one or more MDG databases 104. The circuitry 202 may be further configured to apply the one or more large language models (LLMs) 106 on the received at least one search query. The one or more LLMs 106 may be pre-trained models. The circuitry 202 of the system 102 may be further configured to determine metadata associated with the at least one search query based on the application of the one or more LLMs 106 on the received search query. The circuitry 202 of the system 102 may be further configured to query the first MDG database 104A of the one or more MDG databases 104 based on the determined metadata to retrieve the first medical data and output the retrieved first medical data.

Certain embodiments of the disclosure may be found in a system, a method, and an electronic device for medical data governance using large language models. Various embodiments of the disclosure may provide the system that may include circuitry configured to receive a user input including at least one search query to retrieve first medical data from one or more medical data governance (MDG) databases. The system may further apply one or more large language models (LLMs) on the received at least one search query. The one or more LLMs may be pre-trained models. The system may further determine metadata associated with the at least one search query based on the application of the one or more LLMs on the received search query. The system may further query a first MDG database of the one or more MDG databases based on the determined metadata to retrieve the first medical data. The system may further output the retrieved first medical data.

In accordance with an embodiment, the system may extract, from the first MDG database, raw data associated with the determined metadata based on querying the first MDG database. The system may further generate one or more constructs associated with the one or more LLMs to be applied on the extracted raw data, wherein the one or more constructs are associated with the determined metadata. The system may further retrieve the first medical data based on the application of the generated one or more constructs on the extracted raw data. The system may further output the retrieved first medical data.

In accordance with an embodiment, the one or more medical data governance (MDG) databases comprises of electronic medical records associated with at least one user.

In accordance with an embodiment, the electronic medical records correspond to at least one of: doctor consultation notes, doctor progress notes, nurses' notes, a prescription history, problem lists, International Classification of Diseases (ICD) codes, laboratory results, pathology reports, X-radiation (X-RAY) reports, computed tomography (CT) reports, magnetic resonance imaging (MRI) reports, ultrasound reports, cardiac catheter reports, or cardiac stress reports associated with at least one user.

In accordance with an embodiment, the system may acquire numerical data captured by one or more medical devices associated with at least one user. The system may further generate a description associated with the received numerical data. The system may further store the generated description in at least one of the one or more MDG databases.

In accordance with an embodiment, the system may receive real-time medical data associated with at least one user from one or more medical devices associated with the at least one user. The system may further determine at least one upcoming event associated with a medical condition of the at least one user based on the received real-time medical data and the one or more MDG databases. The system may further output the determined at least one upcoming event.

In accordance with an embodiment, the system may determine at least one keyword from the determined metadata. The at least one keyword is associated with the at least one search query. The system may further select the first MDG database of the one or more MDG databases based on the determined at least one keyword. The system may further query the selected first MDG database of the one or more MDG databases.

In accordance with an embodiment, the at least one keyword corresponds to one of a name of a user, a name of a medical facility, a name of a disease, or a name of a medical procedure.

As utilized herein, the term "exemplary" means serving as a non-limiting example, instance, or illustration. As utilized herein, the terms "for example," and "for example" set off lists of one or more non-limiting examples, instances, or illustrations. As utilized herein, circuitry is "operable" to perform a function whenever the circuitry comprises the necessary hardware and/or code (if any is necessary) to perform the function, regardless of whether performance of the function is disabled, or not enabled, by some user-configurable setting.

The terminology used herein is for the purpose of describing particular embodiments only and is not intended to be limiting of embodiments of the disclosure. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Further, many embodiments are described in terms of sequences of actions to be performed by, for example, elements of a computing device. It will be recognized that various actions described herein can be performed by specific circuits (for example, application specific integrated circuits (ASICs)), by program instructions being executed by one or more processors, or by a combination of both. Additionally, these sequences of actions described herein can be considered to be embodied entirely within any non-transitory form of computer readable storage medium having stored therein a corresponding set of computer instructions that upon execution would cause an associated processor to perform the functionality described herein.

Thus, the various aspects of the disclosure may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Another embodiment of the disclosure may provide a non-transitory machine and/or computer-readable storage and/or media, having stored thereon, a machine code and/or a computer program having at least one code section executable by a machine and/or a computer, thereby causing the machine and/or computer to perform the steps as described herein for generating a novel molecular structure using a protein structure.

The present disclosure may also be embedded in a computer program product, which comprises all the features enabling the implementation of the methods described herein, and which when loaded in a computer system is able to carry out these methods. Computer program in the present context means any expression, in any language, code or notation, either statically or dynamically defined, of a set of instructions intended to cause a system having an information processing capability to perform a particular function either directly or after either or both of the following: a) conversion to another language, code or notation; b) reproduction in a different material form.

Further, those of skill in the art will appreciate that the various illustrative logical blocks, modules, circuits, algorithms, and/or steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The methods, sequences and/or algorithms described in connection with the embodiments disclosed herein may be embodied directly in firmware, hardware, in a software module executed by a processor, or in a combination thereof. A software module may reside in RAM memory, flash memory, ROM memory, EPROM memory, EEPROM memory, registers, hard disk, physical and/or virtual disk, a removable disk, a CD-ROM, virtualized system or device such as a virtual server or container, or any other form of storage medium known in the art. An exemplary storage medium is communicatively coupled to the processor (including logic/code executing in the processor) such that the processor can read information from, and write information to, the storage medium. In the alternative, the storage medium may be integral to the processor.

While the present disclosure has been described with reference to certain embodiments, it will be noted understood by, for example, those skilled in the art that various changes and modifications could be made and equivalents may be substituted without departing from the scope of the present disclosure as defined, for example, in the appended claims. In addition, many modifications may be made to adapt a particular situation or material to the teachings of the present disclosure without departing from its scope. The functions, steps and/or actions of the method claims in accordance with the embodiments of the disclosure described herein need not be performed in any particular order. Furthermore, although elements of the disclosure may be described or claimed in the singular, the plural is contemplated unless limitation to the singular is explicitly stated. Therefore, it is intended that the present disclosure is not limited to the particular embodiment disclosed, but that the present disclosure will include all embodiments falling within the scope of the appended claims.

The present invention introduces a fundamentally new paradigm for the decentralized, policy-constrained, and audit-ready governance of persona agents in regulated environments such as healthcare. Unlike conventional approaches, which rely on centralized control, static credential verification, or post hoc auditing, this invention enables prompt-driven, real-time instantiation and supervision of persona agents directly on a mesh of computing nodes, each equipped with robust policy enforcement, credential lineage validation, and privacy-compliant session memory management.

The system's metadata-driven governance pipeline uniquely captures and attaches all relevant context—including initiator identity, credential and institutional affiliation, geo-location, model instance accreditation, privacy flags, and complete delegation chains—to every prompt and agent session. This facilitates continuous, context-aware policy constraint evaluation and credential validation for every agent action, supported by real-time gating and dynamic escalation to supervisory review for high-risk or policy-sensitive operations.

The invention's mesh architecture empowers a plurality of computing nodes to autonomously instantiate and manage persona agents, each node maintaining a local policy engine, cryptographically chained audit ledger, and the ability to communicate via secure peer-to-peer channels. Mesh-wide management enables dynamic workload balancing, seamless failover and fallback using pre-authorized role tokens, and offline operation with later audit synchronization—providing unparalleled operational resilience and continuity even during device failures or network outages.

By implementing a credential hierarchy map and recursion detector, the system actively prevents unauthorized, cyclical, or recursive delegation among persona agents, ensuring that all delegation chains remain compliant with institutional and regulatory requirements. Every action, delegation, credential check, and policy decision is immutably recorded in a tamper-evident, distributed audit ledger, forming a composite audit graph for full forensic traceability and regulatory reporting.

The inclusion of federated compliance tokens allows for secure, auditable, and policy-bound workflows across institutional or jurisdictional boundaries, with remote token validation and policy enforcement at the receiving node. Session memory governance modules enforce strict privacy, time, or token-bound memory windows, ensuring that agents retain no data beyond permitted limits.

These advances deliver a level of technical sophistication, operational robustness, privacy protection, compliance, and auditability previously unattainable in AI agent systems. The invention's modular, standards-compliant design allows for rapid adaptation to new domains, regulatory regimes, and device classes—enabling safe, effective, and transparent deployment of persona agents in any compliance-critical environment. All elements of claims 1-20 are thus harmonized and fully enabled by the disclosed system and method.

A particular advantage of the invention is its guarantee of cryptographically verifiable, atomic state transition and audit synchronization across all mesh nodes-even in the presence of network partitions, operational failover, or node re-merge events. This ensures continuous, gap-free compliance, traceability, and policy enforcement regardless of network topology or temporary isolation.

The invention's mesh architecture (FIGS. 11 and 12) delivers prompt-driven persona-agent instantiation directly on Edge Devices, where the Metadata Filter & Enrichment Engine attaches credential lineage, institutional affiliation, geo-location, LLM-instance accreditation, privacy flags, policy context, and the complete delegation chain to every prompt. This exhaustive context lets the Policy Constraint Engine and gating logic enforce real-time, fine-grained controls while the credential hierarchy map and recursion detector block unauthorized or cyclical delegation. Because each computing node hosts its own local policy engine and cryptographically chained audit ledger, agent operation remains compliant and uninterrupted during network partitions, with peer-to-peer fail-over managed by the fallback control module and validated through secure communication channels.

As used herein, a 'single computing node' or 'single computing instance' refers to any individual hardware or virtualized environment, including but not limited to a physical server, a virtual machine, a software container, or a cloud-based instance, regardless of the number of physical processors or cores and regardless of deployment location.

Beyond resilience, the invention guarantees verifiable compliance. Session-memory governance modules impose token- or time-bounded windows that automatically expire, reset, or truncate agent context, protecting privacy and aligning with evolving regulations. Every agent action, policy decision, delegation event, and Supervisor Review Interface outcome is immutably recorded in a composite audit graph that synchronizes across the mesh, providing regulator-ready transparency even offline. When workflows cross institutional boundaries, federated compliance tokens signed by the Digital-Signature Module carry policy snapshots and credential provenance to the receiving node, where the Token Validator reenforces policy before spin-up. Together, the metadata-driven governance pipeline, distributed audit, real-time policy enforcement, and seamless cross-institution operation supply a level of operational robustness, privacy protection, and auditability unattainable in centralized or post-hoc systems.

In sum, the invention delivers comprehensive, real-time, policy-bound, and distributed governance of AI persona agents—achieving a level of operational resilience, compliance, auditability, privacy, and technical sophistication not possible with centralized, monolithic, or static prior art.

What is claimed is:

1. A computing system for real-time governance, supervision, and audit of persona agents in a regulated environment, the system comprising:

at least one computing node including processor circuitry, memory, and a network interface, the computing node comprising;

a User-Prompt Interface to receive a prompt generated by an initiator;

a Metadata Filter & Enrichment Engine stored in the memory and executable by the processor circuitry, the Metadata Filter & Enrichment Engine attaches, to each received prompt, structured metadata comprising one or more of credential information, institutional affiliation, geographic location, language-model-instance accreditation, privacy flags, risk classification, policy context, and a delegation chain;

a Persona Role Constructor to instantiate, on the computing node, a persona agent bound by the attached metadata;

a Policy Constraint Engine to evaluate every contemplated action of the persona agent against institutional, regulatory, jurisdictional, and risk-based policy constraints;

a gating logic module, coupled to the Policy Constraint Engine, to (i) freeze execution of a contemplated action of the persona agent when the Policy Constraint Engine detects that the contemplated action generated by the persona agent exceeds an authorized policy threshold, and (ii) invoke a Supervisor Review Interface that allows a credentialed human or digital supervisor to approve, modify, or reject the frozen contemplated action;

a Session Memory Governance Module to enforce a session-memory window that expires, resets, or truncates agent context based on token limits, time limits, policy change, or credential revocation;

an Audit Logging Subsystem to generate and store audit records of prompt receipt, agent instantiation, policy evaluations, supervisory decisions, delegation events, memory-window events, and agent outputs;

a Fallback Control Module to monitor device availability and, upon detection of a failure-state indicator, issue a cryptographically signed role-switch token that authorizes a peer computing node to assume operational responsibilities while maintaining credential lineage and audit continuity;

a peer-to-peer communication channel through which the computing node synchronizes its data with peer computing nodes.

2. The system of claim 1, wherein the Metadata Filter & Enrichment Engine attaches the metadata fields to the prompt immediately upon receipt and before any processing by the persona agent.

3. The system of claim 1, wherein the Policy Constraint Engine consults a credential hierarchy map and a recursion detector to detect and block unauthorized, cyclical, or recursive delegations among persona agents.

4. The system of claim 1, wherein the gating logic module pauses persona-agent execution and routes the contemplated action to the Supervisor Review Interface for approval, modification, or rejection, and records the supervisory decision in the cryptographically linked audit ledger.

5. The system of claim 1, wherein the Session Memory Governance Module also deletes or obfuscates retained context upon expiration of the session-memory window to comply with privacy flags in the attached metadata.

6. The system of claim 1, wherein the Audit Logging Subsystem appends each audit record to a cryptographically linked, tamper-evident audit ledger maintained locally on the computing node, and wherein audit records are immutable and auditable.

7. The system of claim 6, wherein the Fallback Control Module issues the role-switch token only after signing the token with a device-specific digital signature and recording the issuance in a cryptographically linked audit ledger.

8. The system of claim 1, wherein all claimed modules are implemented on a single computing node or instance, including but not limited to a physical server, virtual machine, or cloud-based instance.

9. The system of claim 1, further comprising a Federated Policy-Token Generator to encapsulate the delegation chain, credential lineage, policy snapshot, and privacy flags into a signed compliance token when a workflow crosses an institutional boundary.

10. The system of claim 9, wherein a receiving institution node includes a Token Validator that compares the signed compliance token to a receiving policy registry and, upon successful validation, authorizes a Persona-Deployment Decision Engine to instantiate a compliant persona agent at the receiving institution.

11. A computer-implemented method performed on a computing node for decentralized, real-time governance, supervision, and audit of persona agents in a regulated environment, the method comprising:

(a) receiving, at a User-Prompt Interface, a natural-language prompt generated by an initiator;

(b) attaching, by a Metadata Filter & Enrichment Engine, structured metadata to the received prompt, the metadata comprising at least one of credential information, institutional affiliation, geographic location, language-model-instance accreditation, privacy flags, risk classification, policy context, and a delegation chain;

(c) instantiating, by a Persona Role Constructor, a persona agent on the computing node using the prompt and the attached metadata;

(d) evaluating, by a Policy Constraint Engine, each contemplated action generated by the persona agent against institutional, regulatory, jurisdictional, and risk-based policy constraints;

(e) freezing execution of a contemplated action, by a gating logic module, of the persona agent when the evaluating step detects that the contemplated action exceeds an authorized policy threshold, and invoking a Supervisor Review Interface to obtain approval, modification, or rejection of the frozen contemplated action;

(f) enforcing, by a Session Memory Governance Module, a session-memory window that expires, resets, or truncates agent context responsive to token limits, time limits, policy change, or credential revocation;

(g) generating and storing, by an Audit Logging Subsystem, audit records of prompts, agent instantiations, policy evaluations, supervisory decisions, delegation events, memory-window events, and agent outputs on the computing node;

(h) monitoring, by a Fallback Control Module, device availability; and upon detection of a failure-state indicator, issuing a cryptographically signed role-switch token that authorizes a peer computing node to assume operational responsibilities while maintaining credential lineage and audit continuity; and (i) synchronizing data with peer computing nodes over a peer-to-peer communication channel.

12. The method of claim 11, wherein the attaching step is performed immediately upon receipt of the prompt and before any processing by the persona agent.

13. The method of claim 11, wherein the evaluating step further comprises consulting a credential hierarchy map and a recursion detector to detect and block unauthorized, cyclical, or recursive delegations among persona agents.

14. The method of claim 11, wherein the freezing execution and invoking steps further comprise recording the supervisory decision obtained from the Supervisor Review Interface in the cryptographically linked audit ledger.

15. The method of claim 11, wherein the enforcing step further comprises deleting or obfuscating retained context upon expiration of the session-memory window responsive to privacy flags in the attached metadata.

16. The method of claim 11, further comprising: appending, by the Audit Logging Subsystem, each audit record to a cryptographically linked, tamper-evident audit ledger maintained locally on the computing node.

17. The method of claim 11, wherein all method steps are performed on a single computing node or instance, including but not limited to a physical server, virtual machine, or cloud-based instance.

18. The method of claim 11, wherein the issuing step further comprises digitally signing the role-switch token with a device-specific signature and recording issuance of the token in a cryptographically linked audit ledger.

19. The method of claim 11, further comprising encapsulating, by a Federated Policy-Token Generator, the delegation chain, credential lineage, policy snapshot, and privacy flags into a signed compliance token when a workflow crosses an institutional boundary.

20. The method of claim 19, further comprising, at a receiving institution node, validating the signed compliance token against a receiving policy registry and, upon successful validation, instantiating a compliant persona agent at the receiving institution.

* * * * *